(12) United States Patent
Scammell

(10) Patent No.: US 8,834,872 B2
(45) Date of Patent: Sep. 16, 2014

(54) USES OF ANTIBODIES

(71) Applicant: A.C.N. 135 493 391 Pty Ltd., Adelaide (AU)

(72) Inventor: Antony William Scammell, College Park (AU)

(73) Assignee: A.C.N 135 493 391 Pty Ltd., Adelaide (AU)

( * ) Notice: Subject to any disclaimer, the term of this patent is extended or adjusted under 35 U.S.C. 154(b) by 0 days.

(21) Appl. No.: 13/927,491

(22) Filed: Jun. 26, 2013

(65) Prior Publication Data

US 2013/0295109 A1 Nov. 7, 2013

Related U.S. Application Data

(63) Continuation of application No. 12/310,643, filed as application No. PCT/AU2007/001282 on Aug. 31, 2007, now abandoned.

(30) Foreign Application Priority Data

Aug. 31, 2006 (AU) .................................. 2006904752

(51) Int. Cl.
| | |
|---|---|
| *A61K 39/395* | (2006.01) |
| *A61K 35/20* | (2006.01) |
| *C07K 16/02* | (2006.01) |
| *C07K 16/04* | (2006.01) |
| *G01N 33/574* | (2006.01) |
| *A61K 35/56* | (2006.01) |
| *C07K 16/28* | (2006.01) |

(52) U.S. Cl.
CPC ................. *C07K 16/28* (2013.01); *A61K 35/20* (2013.01); *C07K 16/02* (2013.01); *C07K 16/04* (2013.01); *G01N 33/57407* (2013.01); *A61K 35/57* (2013.01); *C07K 16/2866* (2013.01)
USPC ..................................... 424/130.1; 424/178.1

(58) Field of Classification Search
None
See application file for complete search history.

(56) References Cited

U.S. PATENT DOCUMENTS

| | | |
|---|---|---|
| 3,911,108 A | 10/1975 | Singh |
| 6,202,546 B1 | 3/2001 | Scammell |
| 6,248,366 B1 | 6/2001 | Scammell |
| 2009/0306347 A1 | 12/2009 | Tsukamoto |
| 2011/0300153 A1 | 12/2011 | Tsukamoto |

FOREIGN PATENT DOCUMENTS

| | | |
|---|---|---|
| CN | 1303889 | 7/2001 |
| CN | 1377694 | 4/2002 |
| WO | WO9814209 | 4/1998 |
| WO | WO9936077 | 7/1999 |
| WO | WO9964069 | 12/1999 |
| WO | WO0226256 | 4/2002 |
| WO | WO 03/080082 | 10/2003 |
| WO | WO 2004/024773 | 3/2004 |
| WO | WO 2005/090406 | 9/2005 |
| WO | WO2006047298 | 5/2006 |
| WO | WO 2006/083936 | 8/2006 |
| WO | WO2007/026689 | 3/2007 |

OTHER PUBLICATIONS

Strome et al., The Oncologist, 2007; 12:1084-95.*
Brand et al., Anticancer Res. 2006; 26:463-70.*
European Search Report for EP07060240 of Nov. 26, 2010.
International Preliminary Report on Patentability for PCT/AU2007/001282 of Mar. 27, 2008.
International Search Report. For PCT/AU2007/001282 of Oct. 25, 2007.
Mao Weiguang. et al., Cancer Research, American Association for Cancer Research, vol. 64, No. 3, p. 781-788, Feb. 1, 2004.
Office Action, CN 200780039676.X, Feb. 29, 2012.
Tachibana, M., et al., "Expression and prognostic significance of EFNB1 and EphB4 genes in patients with oesophageal squamous cell carcinoma" Dig Liver Dis. 39, p. 726-732, 2007.
Wang Jian-Dong, et al., Oncology, vol. 73, No. 3-4, p. 233-245, Jan. 1, 2007.

* cited by examiner

*Primary Examiner* — Sheela J Huff
(74) *Attorney, Agent, or Firm* — Hueschen and Sage

(57) ABSTRACT

The present invention provides a method of preparing an antibody containing milk or egg product for use in preventing and/or treating of a non infectious medical condition. The invention also provides non-systemic modes of administering pharmaceutical compositions including the antibody containing milk or egg products, including to the GI tract.

4 Claims, 6 Drawing Sheets

Figure 4

SEQ ID NO:1 – Human EphB4 protein sequence

```
  1 melrvllcwa slaaaleetl lntkletadl kwvtfpqvdg qweelsqlde eqhsvrtyev
 61 cdvqrapgqa hwlrtqwvpr rgavhvyatl rftmleclsl pragrscket ftvfyyesda
121 dtataltpaw menpylkvdt vaaehltrkv pgaeatgkvn vrtlrlgpls kagfylafqd
181 qgacmallsl hlfykkcaql tvnltrfpet vprelvvpva gscvvdavpa pgpspslycr
241 edgqwaeqpv tgcscapgfe aaegntkcra caggtfkpls gegscqpcpa nshsntigsa
301 vcqcrvgyfr artdprgapc ttppsaprsv vsrlngsslh lewsaplesg gredltyalr
361 crecrpggsc apcggdltfd pgprdlvepw vvvrglrpdf tytfevtaln qvsslatgpv
421 pfepvnvttd revppavsdi rvtrsspssl slawavpnap sgavldyevk yhekqaegps
481 svrflktsen raelrglkrg asylvqvrar seagygpfgq ehhsqtqlde eqwreqlal
541 iagtavvgvv lvlvvivvav lclrkqsngr eaeysdkhgq ylighqtkvy idpftyedpn
601 eavrefakel dsyvkieev igageefgevc rgrlkapgkk escvaiktlk qgytergrre
661 flseaslmgq fehpnilrle qvvtnsmpvm iltefmenga ldsflrlndg qftviqlvgm
721 lrgiasgmky laemsyvhrd laarnilves nlvckvsdfg lsrfleenss dptytsslgg
781 klpirwtape alafrkftsa sdawsygiva wevmstgerp ywdmsnqdvi naieqdyrlp
841 pppdcptslh qlmldcwqkd rnarprfpqv vsaldkmirn paslkivaro nggashplla
901 qrqphysafg svgewlraik mqryeesfaa agfgsfelvs qisaediiri qvtlaqhqkk
961 ilasvqhmks qakpgtpgg qgpapqy
```

Figure 5

SEQ ID NO:2 – Murine EphB4 protein sequence

```
  1 melrallcwa slataleetl lntkletadl kwvtypqaeg qweelsglde eqhsvrtyev
 61 cdmkrpgqqa hwlrtqwvpr rgavhvyati rftmmeclsl prasrscket ftvfyyesea
121 dtatahtpaw menpyikvdt vaaehltrkr pqaeatgkvn iktirigpls kagfylafqd
181 qgacmallsl hlfykkcswl itnltyfpet vprelvvpva qscvanavpt anpspslycr
241 edgqwaeqqv tgcscapgye aaesnkvcra cgqgtfkpqi gdesclpcpa nshsrnigsp
301 vclcrigyyr arsdprsspc ttppsaprsv vhhlnqstlr lewsaplesq qredltyavr
361 crecrpggsc lpcggdmtfd pgprdlvepw vairqlxpdv tytfevaaln qvstlatgpp
421 pfepvnvttd revppavsdi rvtrsspssl ilswalprap sgavldyevk yhekgaegps
481 svrflktsen raelrglkrg asylvpvrar seagygpfgq ehhsqtqlde seswreqlal
541 iagtavvgvv lvlvvviiav lcfrkqsygr eveysdkhgq ylighgtkvy idpftyedpn
601 eavrefakei dvsyvkleev iqagefgevc rgrlkapgkk escvaiktlk ggyterqrre
661 flseasimgq fehpniirle gvvtnsvpvm iltefmenga idsflrlndg qftviqlvqm
721 lrgiasgmry laemsyvhrd laarnilvns nlvckvsdfg larfleenss dptytsslgg
781 kipirwtape aiafrkftsa sdawsygivm wevmsfgerp ywdmsnqdvi naieqdyrlp
841 pppdcptslh qlmldcwqkd rnarprfpqv vsaldkmirn paslkivare nggashplld
901 qrqphysafg svqewlraik mgryeesfaa agfgsfevvs qisaedllri gvtlaghqkk
961 ilasvqhmka qakpqapggt ggpaqqf
```

Figure 6

SEQ ID NO:3 – Bovine EphB4 protein sequence

```
  1 melrallcwa slaaaleetl lntkletadl kwvtfpqadg qweelsglde eqhsvrtyev
 61 cdmqrapgla hwlrtgwvpr rqavhvyatl rftmleclsl pragrscket ftvfyfesda
121 dtatahtpaw menpyikvdt vaaehltrkr pgaeatgkvn vktlrlgplt kagfylafqd
181 qgacmallsl hlfykkcaqq tvnltyfpet vprelvvpva gscvadampa pgpspslycr
241 edgqwaeqpv tgcscnagfe aaegntkcra caqgtfkpls gegscqpcpa nshsnaigss
301 icqcrlgyfr astdprsapc ttppsaprsv vprlngsalr lewsaplesg gredltyalr
361 crecrpggsc tpcgqdltfd pgprdlvepw vairylrpdv tytfevtaln qvsslasgpv
421 pfeavnvttd revpppvsdi rvtrsspssl slawavprap sgavldyevk yhekqaegps
481 svrflktsen raelrglkrg asylvqvrar seagygpfgq ehhsqtqlde netwreqlal
541 iagtaavgvv lvlvviviav lclrkqsngr eaeysdkhaq ylighgtkvy idpfttyedpn
601 eavrefakei dvsyvkieev igageigevc rgrlkapgkk escvaiktlk ggyterqrre
661 flseasimgq fehpniirle qvvtnsvpvm iltefmenca ldsflrlndg qftviqlvgm
721 lrgiasqmry laemsyvhrd laarnilvns nlvckvsdfg lsrfleenss dptytsslgg
781 kipirwtape aiafrkftsa sdawsyqivm wevnsfgerp ywdmsnqdvi naieqdyrlp
841 pppdcptslh qlmldcwqkd rnarprfpqv vsaldkmirn paslkivare nggashplld
901 qrqphysafg svgewlraik mgryeesfaa agfgsfelvs qistedllri gvtlaghqkk
961 ilasvqhmks qakpgapqgs qapapqy
```

USES OF ANTIBODIES

FIELD OF THE INVENTION

The present invention relates to the treatment and/or prevention of non-infectious medical conditions using antibody-containing compositions, preferably by topical application. In particular embodiments the present invention relates to methods of treatment and/or prevention of cancer or non cancer or hyperproliferative diseases including the step of administering an antibody-containing milk and or egg product, preferably by topical application.

BACKGROUND TO THE INVENTION

The treatment of many serious medical conditions is almost exclusively performed systemically. However, there are certain medical conditions for which non-systemic (including topical) treatment may be more suitable, such as conditions including, but not limited to, those affecting the skin, the gastrointestinal (GI) tract (including the oropharynx), the eye, ear, nasopharynx, bladder, vagina and cervix.

Skin cancers account for around 81% of all new cancers diagnosed each year in Australia. There are three main types of skin cancer: basal cell carcinoma and squamous cell carcinoma (also known as non-melanoma skin cancers) and melanoma. Non-melanoma skin cancer is the most frequently occurring cancer in Australia (over 374,000 new cases each year), but the least life-threatening, although some cases can be fatal.

GI cancers include a large variety of cancers including colorectal cancers. Globally, colorectal cancer (cancer of the large bowel) is the third most common cancer in men and women, representing 13% of all cancers. In Australia, it is the second most common cancer in both men and women. About 20 percent of patients have metastatic disease (spreading beyond the large bowel) at the time of diagnosis, and 50 percent of all colorectal cancer patients will develop metastases and ultimately die from their disease. About 56,000 people die from colorectal cancer every year in the US and the mortality rate in Europe exceeds 100,000 patients per year.

Colorectal cancers are solid tumours (growths) which start in the innermost layer (that is the endothelial lining) of the intestine and can grow through some or all of the other layers. Colon cancers arise from benign neoplasms and evolve into adenocarcinomas through a stepwise histological progression sequence, proceeding from either adenomas or hyperplastic polyps/serrated adenomas.

Colorectal cancer usually begins with the growth of polyps. In 1994, more than 2,000,000 colonoscopies were performed in the US and over 650,000 of these patients underwent polypectomy. Early detection and removal of polyps significantly reduces the incidence of colorectal cancer. However, about 50 percent of people aged 60 will have at least one adenomatous (potentially cancerous) polyp of 1 cm diameter or greater.

Since a large proportion of patients presenting with colorectal cancer present at a late stage in the disease it would be desirable to have a treatment which could aid in the prevention and/or treatment of colorectal cancer without the need for surgery, or to reduce the risk of recurrence after surgery, for instance after a polpectomy.

Oesophageal cancer is now the ninth most common cancer in adults in the UK. A precursor condition of oesophageal cancer is Barrett's oesophagus. In Barrett's oesophagus, the cells lining the oesophagus change to resemble the cells lining the stomach. It may develop following long-term acid reflux from the stomach. People with Barrett's oesophagus are 125 times more likely to develop oesophageal cancer than the average person.

Head and neck cancer, including oral and pharyngeal cancer, is the sixth most common malignancy reported worldwide and has very high mortality ratios for all malignancy types. About 90 percent of head and neck cancers are of the squamous cell variety. Although there have been significant improvements in chemotherapy and surgical techniques, the disease is often particularly challenging to treat since most patients present with advanced disease, have secondary tumours and suffer from other co-morbidities.

Bladder cancer is the fourth most common cancer in men, with more than 10,000 people diagnosed with the disease each year in the UK. Bladder cancer is rare in people under 40; the average age at diagnosis is 65. By the time of diagnosis, about 85% of bladder cancers are still limited to the bladder. Bladder cancer usually starts in the mucosa and, for a while, only grows towards the inside of the bladder.

Cancers of the eye are not common, but are a serious set of conditions which require effective methods of treatment and prevention. Cancers can occur in all parts of the eye. The most common malignant primary intraocular tumor in adults is melanoma. Though most attention is given to posterior choroidal melanoma, these tumors can also occur in the iris and ciliary body. The most common eyelid cancer is basal cell carcinoma. This cancer can grow around the eye but rarely spreads to other parts of the body. Other types of common eyelid cancers include squamous carcinoma, sebaceous carcinoma and malignant melanoma.

Uterine cancer is the most common gynaecological cancer. Most cancers of the uterus are cancers of the lining of the uterus (the endometrium). Cancers can also develop in the muscle layers of the uterus. Other, less common, types of cancer of the uterus are adenosquamous carcinoma, papillary serous carcinoma and, rarely, clear cell carcinoma or uterine sarcoma. These cancers are aggressive and are more likely to metastasise. Cervical cancer, although less common than uterine cancer, typically begins in the squamous cells that cover the outer surface of the cervix.

It would be desirable to have a treatment which could aid in the prevention and/or treatment of the above, and related, conditions without the need for surgery, or to reduce the risk of recurrence after surgery.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

The present invention is based on an antibody-containing milk or egg product which is suitable for use in treating a non-infectious medical condition preferably by topical application.

In a first aspect the present invention provides a use of an antibody-containing milk or egg product for the manufacture of a medicament for the prevention and/or treatment of a non-infectious medical condition. This aspect of the invention also provides a method of preparing a medicament in the form of a food, specialty nutritional or pharmaceutical product for the prevention and/or treatment of a non-infectious medical condition, the method including vaccinating a mammal or bird so that an antibody-containing milk or egg product is produced. In one form of the invention the mammal is selected from the group consisting of: a bovine, an ovine, a porcine and a caprine. In another form the bird is selected from the group consisting of chicken, goose and duck. In other forms of the invention the step of vaccinating involves administering an immunogenic protein or peptide to the mammal or bird, wherein the immunogenic protein or peptide is capable of eliciting an immune response to a mammalian-derived molecule, including, but not limited to, a molecule found on the surface of a mammalian cell, such as, but not limited to, a cancer cell.

In a second aspect the present invention provides a method for preventing and/or treating a non-infectious medical condition in a patient including the step of administering to the patient an antibody-containing milk and or egg product. In one form of the invention the milk and or egg product contains antibodies directed to a mammalian-derived molecule, including, but not limited to, a molecule found on the surface of a mammalian cell, such as, but not limited to, a cancer cell.

In a third aspect the present invention provides a method of preparing an antibody-containing milk or egg product for the prevention and/or treatment of a non-infectious medical condition, the method including the step of vaccinating a mammal or bird with an immunogenic protein or peptide.

The invention provides antibodies, nutritional and pharmaceutical compositions and kits including an antibody-containing milk and/or egg product according to the present application and/or antibodies raised according to the methods of the present application.

The present invention also provides the use of anti-EphB4 antibodies for use in the treatment and/or prevention of oesophageal conditions as well as in the diagnosis and monitoring of such conditions. In certain forms of the invention, a method of diagnosing an oesophageal condition, includes determining EphB4 expression in an oesophageal sample, wherein detection of increased EphB4 expression relative to a normal oesophageal sample is indicative the presence of the oesophageal condition. In certain embodiments the oesophageal condition is selected from the group consisting of Barrett's oesophagus and oesophageal cancer. The present invention also provides a kit for performing this method.

The present invention also provides the use of anti-EphB4 antibodies in treating and/or preventing colorectal polyps and in post operative treatment following polypectomy in colorectal cancer.

BRIEF DESCRIPTION OF THE FIGURES

FIG. 4 shows the protein sequence of human EphB4 (SEQ ID NO:1).

FIG. 5 shows the protein sequence of murine EphB4 (SEQ ID NO:2).

FIG. 6 shows the protein sequence of bovine EphB4 (SEQ ID NO:3).

DETAILED DESCRIPTION OF THE INVENTION

Figure 1:
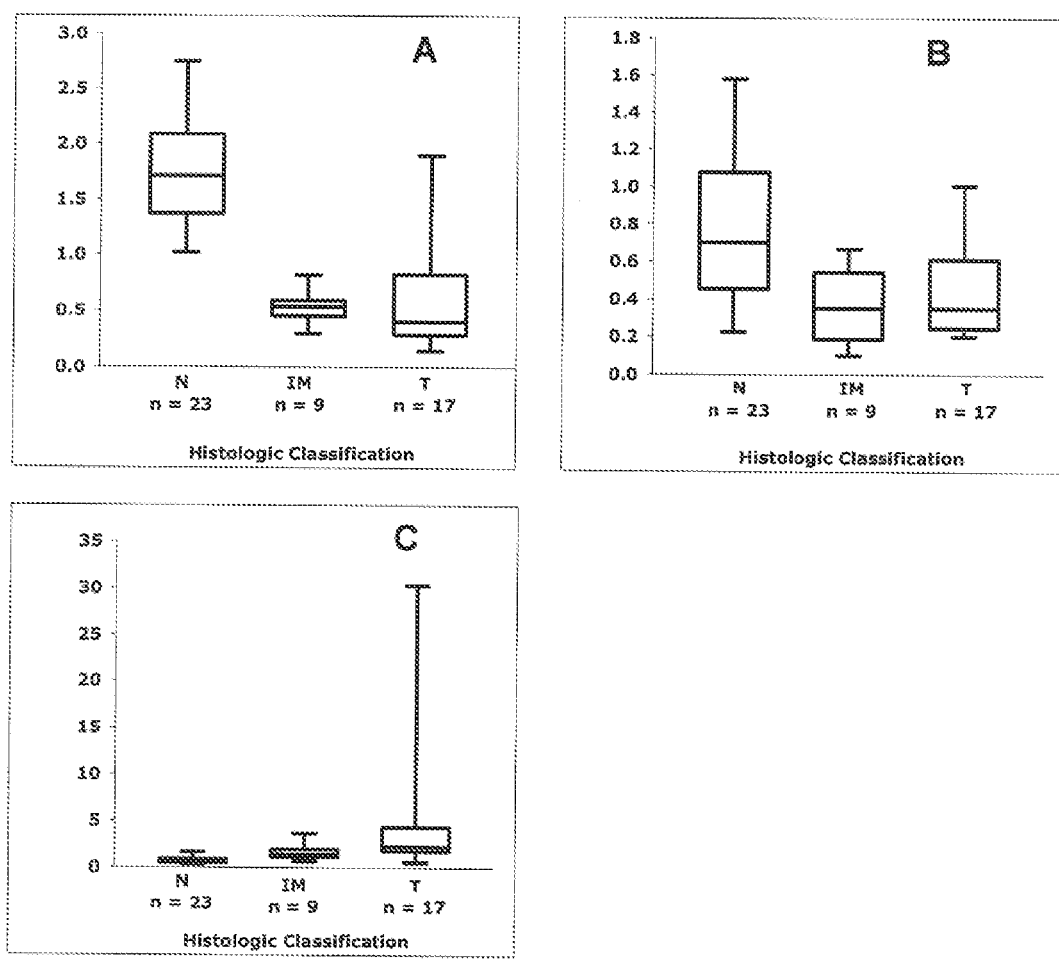
FIG. 1 shows the relative EphA1 (A), EphA2 (B) and EfnA1 (C) mRNA levels in the different histological groups. The boxes show the 25th and 75th percentile (interquartile) ranges. Median values are shown as a horizontal bar in each box. The whiskers show levels outside the 25th and 75th percentile. An asterisk (*) represents $p<0.017$ vs. normal.

The present invention seeks to provide a method of treating and/or preventing non-infectious medical conditions by non-systemic administration of a biologically active agent. For example, applying an anticancer agent directly to a cancer would be more convenient than undergoing systemic treatment. In the case of GI conditions and cancers, administration of the biologically active agent via the lumen of the GI tract would be more convenient than undergoing systemic treatment. In GI cancer for example, the biologically active molecules should specifically target any aberrant cells lining the GI tract and prevent their proliferation.

It is commonly accepted that all types of cancer treatment have some side effects. It is considered that monoclonal antibodies, to be administered systemically, have fewer side effects than other treatments because they are developed from proteins that occur naturally in the body and should target specific cells and should not attack non-target cells. However, systemic administration of antibodies is often associated with side effects such as fever, chills and shivering, nausea, itchy rash, headache; and in some cases wheezing and a drop in blood pressure.

Non-systemic treatment, including topical treatment, of disease is desirable to directly target diseased cells and to reduce side-effects and to substantially prevent medications adversely affecting non-target tissues. While not all medical conditions are amenable to topical treatment, certain non-infectious medical conditions affecting the skin, GI tract, the eye, ear, nasopharynx, bladder, vagina and cervix are particularly suited to treatment in this manner.

Materials within the lumen of the GI tract and the nasopharynx effectively remain outside the body and are prevented from escaping into the remainder of the organism by the integrity of the GI tract and nasopharnyx. This integrity is provided by the tight junctions found between the cells lining these parts of the body. The present invention takes advantage of this separation, and of the similar respective barriers found in the bladder, the eye, vagina, uterus and cervix which permits treatment of a specific target without impinging on other parts of the body. For example, when treating a condition with a biologically active agent in a systemic manner, a balance needs to be made between an effective dose and a dose which will result in significant effects on non-target sites throughout the body. This limitation is greatly reduced by the methods of the present invention.

The skin similarly provides a barrier between the inside of the body and the outside. Therefore application of biologically active agents directly to skin conditions provides similar advantages over systemic administration of agents.

Antibodies in particular are large molecules that are generally not able to pass intact through the GI tract, skin, the lining of the bladder, the cornea or through mucous membranes such as those lining the vagina and cervix. Accordingly, administration of antibodies to a patient is usually done parenterally, such as, but not limited to subcutaneous, intramuscular, or intravenous. Such modes of administration permit intact molecules to enter the body and be delivered throughout the body in a systemic manner. Some small molecules may be delivered systemically via oral administration, however, the present invention relates to antibodies and related molecules that require methods such as injection to enter the body intact and functional.

At present, a number of research groups and companies are developing milk-administered products for prophylaxis of various GI tract infections caused by such infectious organisms as *Clostridium difficile, Cryptosporidium, E. coli*, rotavirus, *H. pylori*, Taiwanese E71 virus, and anthrax by hyperimmunising cows with vaccines to raise antibodies against these infections. However, all these products are intended for use in the prevention or treatment of infections. The present invention looks beyond such infection control applications and provides a solution to a problem not yet addressed in the art, that is, a simple and effective prevention and/or treatment approach for non-systemic treatment of non-infectious medical conditions including, but not limited to, cancer, precancerous conditions and non-cancerous conditions, such as hyperproliferative disease. Hyperproliferative diseases or pre-cancerous conditions affecting epithelial cells, such as psoriasis, vitiligo, atopic dermatitis, or hyperproliferative or UV-responsive dermatoses are also suitable candidates for prevention and or treatment according to the methods of the present invention.

The present invention provides an antibody-containing milk and or egg product which may be used in the treatment and/or prevention of a non-infectious skin, GI tract, eye, ear, nasopharynx, bladder, vagina, uterus or cervix condition.

It is the fact that colorectal cancers generally begin as polyps which are accessible from the lumen of the GI tract that provides an opportunity for non-systemic approaches to the treatment of this disease. Some other cancers and non-cancerous conditions of the GI tract may also be vulnerable to this approach. An example of a non-cancerous GI condition for which the present invention may be useful is Barrett's oesophagus (discussed below).

As used herein, the term "antibody" is intended to encompass all forms and fragments of antibodies, including, but not limited to: mammalian antibodies, avian antibodies, monoclonal antibodies, polyclonal antibodies, multispecific antibodies, chimeric antibodies, single chain antibodies, humanized antibodies and fragments thereof. For example, fragments of antibodies include, but are not limited to Fv, Fab, Fab', F(ab')$_2$, and CDRs (complementarity determining regions). Also encompassed are antibodies of all immune classes including, but not limited to: IgA, IgE, IgG, IgM and IgY. Further encompassed are degradation products and fragments of antibodies which maintain their ability to bind antigen in a specific manner. Degradation may be performed as, for example, the antibody passes along a GI tract.

As used herein, the term "molecule on the surface of a mammalian cell" is intended to encompass proteins which normally exist on the extracellular surface of a cell of a mammal, or at least present a portion of the protein on the extracellular surface of the cell, for example a transmembrane protein.

Such proteins may include post-translational modifications which are capable of eliciting an immune response. Typical post-translational modifications include, but are not limited to: glycosylation and phosphorylation. The molecules of themselves may not be immunogenic due to their small size, but methods such as conjugation to a carrier protein can be employed to increase immunogenicity to the relevant mammalian molecule. The molecule may also be a mutated form of the protein which normally exists on the extracellular surface As used herein, the term "GI tract" is intended to encompass the nasopharynx, oral cavity, oesophagus, stomach, duodenum, small intestine, large intestine (colon), rectum and anus.

As used herein, the term "non-infectious medical condition" is intended to encompass conditions including, but not limited to: cancer, precancerous conditions, non cancer hyperproliferative diseases and abnormal growth of "self" cells. In particular embodiments of the present invention, a cancer may be a GI cancer or a skin cancer. Abnormal growth of cells may encompass conditions such as, but not limited to, Barrett's oesophagus, psoriasis, vitiligo, atopic dermatitis, and hyperproliferative or UV-responsive dermatoses. Encompassed by this term are both inflammatory and non-inflammatory conditions. Many inflammatory diseases are known to the skilled addressee, these include, but are in no way limited to the following: migraine, rheumatoid arthritis, asthma, inflammatory bowel disease, motion sickness, induced vomiting, pain, headache, migraine, multiple sclerosis, cardiovascular changes, oedema, asthma/bronchial hyperreactivity and other respiratory diseases including allergic rhinitis, inflammatory diseases of the gut including ulcerative colitis and Crohn's disease, ocular injury and ocular inflammatory diseases. Non-inflammatory conditions include, but are in no way limited to the following: fibromyalgia and non-inflammatory neuropathy.

As used herein, the term "non-infectious" is intended to encompass conditions which have not been caused by invasion or transmission of an exogenous entity. The entity causing the condition in a non-infectious condition is generally an integrated entity and incapable of invasion to other cells.

As used herein, the term "GI cancer" is intended to encompass all cancers arising in, and impinging on, the GI tract. These cancers include, but are not limited to: anal cancer, bile duct cancer, colorectal (colon and/or rectal) cancer, oesophageal cancer, gall bladder cancer, gastric cancer, liver cancer (hepatoma), pancreatic cancer and small intestine cancers and cancers of the oropharynx, mouth, tongue and nose. Of these, the cancers most suitable for treatment according to the methods of the present invention are those accessible directly from the lumen of the GI tract or that encroach upon the lumen of the GI tract. Also encompassed are cancers emanating from internal organs that metastasize in the GI tract or other organs that are able to be treated topically.

As used herein, the terms "non-cancerous" and "precancerous" are intended to encompass non-infectious medical conditions for which treatment is desirable but are not cancers. For example, a condition such as Barrett's oesophagus is a condition in which abnormal cells develop on the inner lining of the lower part of the oesophagus possibly due to reflux of stomach contents into that region of the oesophagus. While Barrett's oesophagus is not a cancerous condition, over a long period of time it can occasionally lead to cancer developing in the lower part of the oesophagus. Accordingly, Barrett's oesophagus may also be considered to be a precancerous condition and its treatment is therefore desirable. The present invention describes for the first time the upregulation of EphB4 in Barrett's oesophagus and this provides a model for describing certain aspects of the present invention.

As used herein, the term "skin cancer" is intended to encompass all cancers arising in the skin. These cancers include, but are not limited to: basal cell carcinoma, squamous cell carcinoma (also known as non-melanoma skin cancer) and melanoma.

As used herein, the term "patient" is intended to encompass humans and animals especially those having or at risk of developing a GI, skin, eye bladder or cervical condition. In most embodiments of the present invention, the patient will be a mammal, and most often a human.

As used herein, the term "administration" is intended to be limited to non-systemic administration such as, but not limited to, topical application, oral administration and ingestion. Also encompassed are forms of direct introduction of the antibody-containing milk or egg product into the GI tract, nose, bladder, eye or vagina/cervix of the patient, for example, directly into the oesophagus as a liquid or into the colon in the form of a suppository or as an enema, or into the bladder via catheter. It would be also possible to prepare a pure immunoglobulin preparation from the antibody-containing milk or egg product, and this could be used to directly apply onto tumour cells, for example, in the colon, in a form of a "colonic-irrigation", in the eye, in the form of an "eye irrigation", or other appropriate procedures. There are many potential formulations for application to skin.

The term "non-systemic administration" is intended to exclude systemic administration routes such as, for example, intravenous administration. Other systemic routes of administration are well known to those of skill in the art.

The amount of antibody required to be administered is described as a "therapeutically effective amount". A "therapeutically effective amount" is that amount which will elicit the biological or medical response of a tissue or system that is being sought. For example, in the case of treating a GI cancer, it is the amount of antibody (included in a nutritional or pharmaceutical matrix) which can delay or prevent the proliferation of GI cancer cells. The "therapeutically effective amount" may also reduce the number of existing GI cancer cells.

In certain embodiments of the present invention, the amount of antibody administered to a patient may be in the order of 0.1 to 30 g dry weight of antibody, per day. In certain applications the amount of antibody to be administered can be calculated using the formula of 0.05 to 2.0 g dry weight of antibody per kilogram of body weight per day. Using this formula an infant may be administered between 0.2 and 5 g dry weight of antibody per day and an adult may be administered between 0.5 and 15 g dry weight of antibody per day.

As used herein, the term "milk product" is intended to encompass all forms of milk from all species of mammal. These forms include, but are not limited to: colostrum, colostrum-derived product, milk and a milk-derived product. Additionally, hyperimmune milk and hyperimmune milk-derived product is also encompassed by the term "milk product". It is generally envisaged that bovines will be the source of the milk product. However, additional species such as, but not limited to, ovines, porcines and caprines may be used.

The term "colostrum" as used herein includes colostral milk; processed colostral milk such as colostral milk processed to partly or completely remove one or more of fat, cellular debris, lactose and casein; and colostral milk or processed colostral milk which has been dried by for example, freeze drying, spray drying or other methods of drying known in the art. Colostral milk is generally taken from a mammal such as a cow within five days after parturition.

As used herein, the term "egg product" is intended to encompass all forms of egg from all avian species. These forms include but are not limited to whole egg, egg yolk, egg or yolk derived product. It is generally envisaged that chickens will be the source of egg product, however additional or alternative species such as but not limited to geese and ducks may also be used.

Other products incorporating antibodies that are intended to be encompassed by the present invention include, but are not limited to: fractionated and/or concentrated immunoglobulin fractions; pure antibody fractions; specific antibody fractions (isolated, for example, by affinity chromatography); long life liquids, spray or freeze dried powders; fresh dairy products; nutritional products with high viscosity eg "sip feeds" to prolong contact time in oropharynx and oesophagus. It is also envisaged that antibodies of the present invention can be incorporated into pharmaceutical compositions and products which allow delivery of the antibodies, in an active form, to the various sites of prevention/treatment, including but not limited to the lower GI tract, eye, bladder, uterus, cervix and skin.

In a first aspect the present invention provides a use of an antibody-containing milk or egg product for the manufacture of a medicament for the prevention and/or treatment of a non-infectious medical condition. This aspect of the invention also provides a method of preparing a medicament for non-systemic administration or food with medicinal benefits for the prevention and/or treatment of a non-infectious medical condition, the method including the step of vaccinating a mammal or bird with an immunogenic protein or peptide so that an antibody-containing milk and or egg product is produced.

The mammal to be vaccinated may be capable of producing commercially viable quantities of milk. It is therefore envisaged that the mammal is selected from the group consisting of: a bovine, an ovine, a porcine and a caprine. The bird to be vaccinated may be capable of producing commercially viable quantities of eggs, therefore chickens, geese or ducks are the most likely.

The step of vaccinating involves administering an immunogenic protein or peptide to the mammal or bird, wherein the immunogenic protein or peptide is capable of eliciting an immune response to a mammalian-derived molecule. In one form of the invention, the mammalian-derived molecule may be found on the surface of a mammalian cell, such as a cancer cell. In other forms of the invention the mammalian-derived molecule may be a mutated protein or a protein which is not normally found on the surface of a mammalian cell.

For the antibody-containing milk or egg product therapy to be successful the milk or egg product ideally should contain high affinity antibodies (immunoglobulins) to the target molecule, therefore it is ideal to produce an antigen that could elicit such a humoral response in the vaccinated mammal or bird, without causing illness to the mammal, its offspring, or the bird.

Vaccination of the mammal or bird involves administration of an antigen which will ideally result in the production of high affinity, selective antibodies to the target molecule. Several procedures could be used to yield a suitable antigen. In one process, pure ligand may be used to purify the target molecule by covalently attaching the ligand to a suitable chromatography matrix and using this to affinity purify the target molecule from a crude cell extract. In another process, the target molecule could be purified using an immunoaffinity purification method, employing a specific polyclonal antibody covalently linked to a suitable chromatography matrix. In yet another process, the target molecule could be produced by a recombinant technology then purified, following standard procedures in the art.

It is envisaged that antibodies directed to molecules on the surface of cancer cells could provide an effective therapy to prevent and/or treat the cancer from which those cells were obtained.

Identification of cancer-specific, cell surface molecules has been the goal of research groups attempting to catalogue the cell surface proteome of various cancer cells. One approach to identify such molecules has been to biotinylate the cell surface then use avidin to capture the biotinylated proteins. The captured proteins are then subjected to identification techniques such as two-dimensional polyacrylamide electrophoresis and/or partial sequencing.

Such research also allows the identification of potential targets for the methods of the present invention. A molecule that shows restricted expression patterns can be of particular interest, especially if it is expressed more on the target population of cells, such as cancer cells. Alternatively, a molecule which has a role in tumorigenesis is also a potential target.

One of the potential target molecules is vascular endothelial growth factor (VEGF), which, although not a cell surface molecule, has a role in tumour angiogenesis. The onset of angiogenesis is believed to be an early event in tumorigenesis and may facilitate tumor progression and metastasis. Several growth factors with angiogenic activity have been described. These include fibroblast growth factors (FGFs), platelet derived growth factor (PDGF) and VEGF. VEGF is a dimeric glycoprotein with structural homology to PDGF. Several variants of VEGF have been described that arise by alternative mRNA splicing. It has been speculated that VEGF may function as a tumour angiogenesis factor in vivo because the expression pattern of VEGF is consistent with a role in embryonic angiogenesis. VEGF mRNA is formed in some primary tumors, VEGF is produced by tumor cell lines in vitro and VEGF mitogenic activity appears to be restricted to endothelial cells. Furthermore, a monoclonal anti-VEGF antibody has been shown to reduce tumour angiogenesis.

Additional antigens that may provide useful targets for the methods of the present invention include molecules that are found on the surface of hyper-proliferating cells. For example, psoriasis is thought to be an autoimmune disease in which T-cells of the immune system recognize a protein/antigen in the skin and attack the area where that protein is found, causing the too-rapid growth of new skin cells and painful, elevated, scaly lesions. These lesions are characterised by hyperproliferation of keratinocytes and the accumulation of activated T-cells in the epidermis of the psoriatic lesions. The skin protein/antigen to which the T-cells are directed may provide a useful target molecule for the methods of the present invention. For example, MUC18 (also known as Mel-CAM or CD146) demonstrates some association with psoriasis as well as some cancers, and thereby provides a potential target. Similarly, other hyperproliferative diseases have specific antigens which may be employed in the methods of the present invention.

A large group of potential target molecules is the Eph receptor family of proteins. The Eph receptors make up the largest subgroup of the receptor tyrosine kinase (RTK) family. RTKs are transmembrane proteins with an extracellular domain capable of recognizing signals from the cells' environment and can influence the growth and survival of cells by acting directly on gene transcription or indirectly on the production of second messengers.

The inventors have identified EphB4 as one example of a potential target for the treatment of a range of cancers that can be treated topically, including some GI, nasopharynx, skin, uterus and bladder cancers (see Examples). Also identified as potential target proteins, within the Eph/ephrin group, are EphB1. EphB2, EfnA1 and EfnB2. The following discussion focuses on EphB4, however, the methodologies described are equally applicable to other members of the Eph/ephrins family, as well as other cell-surface molecules.

EphB4 binds to ephrin-B1 and B2 and may have a role in events mediating differentiation and development. It is abundantly expressed in placenta and in a range of primary tissues and malignant cell lines. EphB4 is expressed in foetal (but not adult) brain, and in primitive and myeloid (but not lymphoid) haematopoietic cells. It is present in several carcinomas: breast (mRNA detected in MCF7, MDA-MB-231, SKBR, T47D, BT20 and BT474 human cell lines), liver, gastrointestinal, leukemia, prostate, lung (down-regulated 3-fold), and melanoma. In one study of EphB4 expression in colon tumour, it was found that expression was upregulated >1.5-fold in 82% (51/62) of samples and >2-fold in 63% (39/62) of samples. It was also overexpressed in ovarian cancer and up-regulated in glioblastoma (>5-fold). However, other studies have shown that EphB4 expression was down-regulated in kidney carcinoma 2.2-fold. In addition, low EphB4 expression in some colorectal cancers has been associated with shorter patient survival times, and there have been reports of variable EphB4 expression in breast cancers. Accordingly, there is no consistent association of EphB4 expression with cancer progression of patient survival.

The results presented in the following Examples show for the first time that EphB4 expression is increased in Barrett's oesophagus and associated oesophageal adenocarcinoma, when compared with the expression level in normal oesophageal tissue. Accordingly, antibodies directed to EphB4 may find application in the prevention and/or treatment of oesophageal conditions, such as Barrett's oesophagus and oesophageal adenocarcinoma. It is further anticipated that EphB4 may provide a marker for indicating the development and/or progression of Barrett's oesophagus and/or oesophageal adenocarcinoma. Accordingly, the present invention provides the use of anti-EphB4 antibodies in the treatment and/or prevention of oesophageal conditions as well as in the diagnosis of such conditions. It is also envisaged that following detection of increased EphB4 expression in the oesophagus of a patient, the patient may be administered anti-EphB4 antibodies in order to prevent or slow the development of conditions such as Barrett's oesophagus and/or oesophageal adenocarcinoma.

Accordingly, the present invention provides a method of diagnosing an oesophageal condition, the method including providing a sample of oesophageal cells from a patient and determining EphB4 expression, wherein detection of increased EphB4 expression relative to a normal oesophageal sample is indicative the presence of the oesophageal condition. In certain embodiments the oesophageal condition is selected from the group consisting of Barrett's oesophagus and oesophageal cancer. It is envisaged that the method of diagnosing also includes monitoring expression of EphB4 in a patient. For example, such monitoring may involve repeated sampling of a patient and determining EphB4 expression as a method of monitoring the patient for disease presence and/or progression. The present invention also provides a kit for performing these methods, including an anti-EphB4 antibody for detecting EphB4 protein expression and/or PCR primers for detecting EphB4 mRNA expression. One such kit envisaged by the present invention is an ELISA-based kit that would allow quantitative or qualitative determination or comparison of EphB4 protein levels in a sample. Various immunological assays can be readily employed by the skilled addressee to detect EphB4 protein expression. A number of companies sell antibodies that could be used to specifically detect EphB4 in oesophageal samples. These methods for performing determining EphB4 levels may include, but are not limited to, immunohistochemistry and densitometry of Western blots used to identify the presence or absence of EphB4. The skilled addressee would be aware of and be able to use alternative methods such as, but not limited to, ELISA and real time RT-PCR. The Examples provided below illustrate the use of PCR to detect EphB4 expression; the skilled addressee could readily prepare primers suitable for the detection of EphB4 expression using standard techniques.

Expression of EphB4 on normal GI epithelial cells is very low, this, coupled with the identification of conformational changes to EphB4 receptors from cancer cells compared with healthy cells, increases the opportunity for safe and effective vaccination of mammals or birds, and for safe and effective prevention and/or treatment of cancer with the milk or egg antibodies. Healthy gut epithelial cells will also generally only express EphB4 below the tight junctions where they are not accessible to topically administered antibodies. For this reason topically applied antibodies to cell surface molecules will have a much safer profile than systemically administered monoclonal antibodies.

The present invention relates to non-infectious medical conditions. In contrast to infectious conditions, non-infectious medical conditions are generally fixed on or in the patient. Being fixed, non-infectious medical conditions are less susceptible to treatment by a passing agent and are therefore more difficult to treat than an infectious condition which usually comprises an infectious entity which is not necessarily attached to the patient. The infectious entity is generally free "living", such as a bacterium or a virus, and is readily susceptible to treatment with, for example, an antibacterial or antiviral agent. The present invention is directed to the more challenging prevention and/or treatment of non-infectious medical conditions without supporting systemic factors generally provided by the immune system.

As noted above, in order to produce milk having high affinity, selective antibodies to the target molecule, the mammal should be vaccinated with a suitable antigen. There are several possible strategies for producing antigen in suitable purity and quantity. A selection of these strategies is described below. It should be noted, however, that these strategies and target proteins are exemplary and that the skilled addressee may know of additional strategies, or variations upon those described below. Furthermore, EphB4 is used simply as an Example of a molecule for which these methods are applicable. The skilled addressee would be able to apply these methods, and the like, to other potential target molecules.

Affinity purification of EphB4 by binding to its ligand requires pure ephrin-B1 and/or B2. Native ephrin B1 ligand can be purified from suitable cells using standard biochemical protein purification techniques, such as, but not limited to; ion or cation exchange chromatography and size exclusion chromatography. Alternatively, the ephrin may be affinity purified by the use of an anti-ephrin antibody. One approach is to prepare a specific immuno affinity column to purify ephrin-B1/B2. A further alternative approach is to use recombinant means to produce large quantities of ephrin-B1/B2. There are published procedures to do this. An advantage of this approach is that only the Eph-binding region of the molecule needs to be produced. Once purified the ephrin or ephrin fragments can be immobilized on a support to permit affinity purification of EphB4 from cell lysates by standard procedures.

Such methodology would yield whole EphB4, with both the extracellular and intracellular portions of the molecule. However, it is only the extracellular portion of the molecule that is relevant as the antigen. The EphB4 molecule is about 120 kDa size, and the extracellular portion of the molecule is about 50 kDa.

An alternative approach to producing large quantities EphB4 is to use recombinant means. As with the ephrin(s), only the extracellular portion of the molecule would need to be produced. As noted above, there are published procedures to do this.

Vaccination of a mammal or bird with a large molecule may not be the most efficient method of producing highly specific antibodies which will have the desired therapeutic effect. Therefore, in order to identify the most suitable antigen for vaccination of the mammal or bird it is necessary to fragment the EphB4 or other target molecule and test antibodies raised to the fragments for their therapeutic effect.

For example, several insolubilised proteolytic enzymes can be used to systematically degrade (hydrolyze) the EphB4 molecule (or extracellular domain thereof). Exemplary enzymes include, but are not limited to: trypsin, pepsin, papain and bromelin. The proteolytic enzyme hydrolysis of EphB4 would yield various peptides, and by using the enzymes individually and in combination would allow the production of overlapping fragments.

One method to produce antibodies to each of the fragments is to purify each fragment individually and immunize test animals with each fragment. Alternatively, a plurality of fragments could be used to vaccinate a single animal, and the resultant antibodies purified from immune serum by affinity chromatography using the individual peptides, where the appropriate antibodies bind to their respective peptides.

It is envisaged that standard laboratory animals would be used for this stage of antigen identification. For example, mice or rabbits could be used for the production of polyclonal antibodies using the fragments of EphB4. Standard protocols for vaccination and purification of antibodies can be used.

The resultant antiserum can be tested in an in vitro cell culture assay, using, for example, human colon cancer cell lines to detect an anti-tumour effect of antibodies to each of the EphB4 fragments. Once an anti-tumour effect is identified the fragment(s) associated with the antibody causing the effect can be identified.

EphB4 fragments or other peptides forming part of target molecules having an anti-tumour or other therapeutic effect may be produced in large quantities using standard procedures such as, but not limited to, recombinant technologies or peptide production and conjugation. These fragments may then be used as the immunogenic peptide (vaccinating antigen) to generate the anti-EphB4 or other specific antibody-containing milk.

It is envisaged that the immunogenic peptide, whether for EphB4 or for other target molecules, will be at least 10 amino acid residues in length. In other forms of the invention, the immunogenic peptide may be at least 20, 30, 40, 50, 60 or 100 residues in length. In further forms of the invention the immunogenic peptide may be a domain of a protein, for example, the extracellular domain of a protein. In certain forms of the invention the length, composition and conformation of the immunogenic peptide may be determined by the degree of sequence homology between the naturally occurring protein found in the mammal or bird and the patient to which the antibody-containing milk or egg product is to be administered.

The cost of a peptide vaccine is likely to be very low in comparison with a viral or bacterial vaccine used for infectious diseases. This may have several advantages over conventional modes of treatment and for therapeutic antibody production, including, but not limited to:

1. Topical treatment with polyclonal antibody containing milk or egg products applied topically will have both cost and safety advantages over monoclonal antibodies applied systemically; and 2. This invention overcomes a difficulty with antibody containing milk or egg products that have proved very expensive to produce. Production of monoclonal antibodies for use in systemic treatment regimens is very expensive in comparison to producing antibody-containing milk or egg products. Furthermore, the methods of the present invention may employ one of a large number of animals to produce the milk or egg product, thereby giving a significantly better chance of producing highly specific and active antibodies against any potential antigen.

Choice of mammal or bird for use in the methods of the present invention will be determined by a number of factors, including amount of antibody-containing milk or egg product required and the level of immune response that can be generated from the selected immunogenic protein or peptide. The level of immune response generated may reflect the degree of sequence homology between the immunogenic protein or peptide and the corresponding sequence in the mammal or bird. The mammal or bird is unlikely to mount an immune response against a "self antigen" because this would be effectively initiating an autoimmune disease. If such a situation were to occur it would be clearly detrimental to the mammal or bird in question. The present invention therefore envisages the requirement for using a variety of species in order to identify a species in which the required immune response is achieved.

It should also be noted that there may or may not be differences between the same target molecule expressed by healthy and diseased cells. If there is a difference, immunogenic peptides incorporating this difference may be used in order to produce an immune response directed to the non-wild type antigen found only in the molecule of a diseased cell. If the diseased cells simply express a higher level of the exact same target antigen than normal cells, careful immunogen selection is required. For example, in some GI tumours there is a difference between the EphB4 expressed in cancer cells and healthy cells. Accordingly, the antibody for use in the methods of the present invention may be raised against an EphB4 peptide that is not represented, either in sequence or structure, in the EphB4 of healthy cells. In cases where EphB4 is simply upregulated, it may be necessary to carefully monitor administration of the antibody to avoid potentially hazardous side-effects. An advantage provided by the present invention is the localized administration of antibodies and this has the potential to dramatically reduce the amount or severity of side-effects and thereby provide greater safety than a systemic approach using monoclonal antibodies, since it is possible to target areas where the diseased cells are present.

The immunogenic peptide may be synthesised by use of a peptide synthesizer. Furthermore, if desired, non-classical amino acids or chemical amino acid analogs can be introduced as a substitution or addition into the polypeptide sequence. Non-classical amino acids include, but are not limited to, the D-isomers of the common amino acids, ornithine, norleucine, norvaline, hydroxyproline, sarcosine, citrulline, homocitrulline, cysteic acid, t-butylglycine, t-butylalanine, phenylglycine, cyclohexylalanine, β-alanine.

If desired, various techniques may be used in order to increase the resultant immune response generated by the immunogenic peptide, in order to develop greater antibody reactivity. For example, the desired peptide may be coupled to another carrier protein including, but not limited to, ovalbumin or keyhole limpet hemocyanin (KLH), and/or through the use of adjuvants including, but not limited to, Freund's complete or incomplete adjuvant.

One exemplary immunogenic peptide that may be used in the methods of the present invention is PVAGSCVVDAVPA-PGPSPSLY (SEQ ID NO:4). This 21 amino acid sequence represents a fragment of the extracellular domain of human EphB4 from cancerous cells. It is envisaged that shorter, longer or different immunogenic peptides could be prepared for EphB4, some of these alternatives have been described in WO2004024773.

It has been found that the sequence shown in SEQ ID NO:4 differs at only two positions from the corresponding bovine sequence (PVAGSCVADAMPAPGPSPSLY, SEQ ID NO:5). Therefore in one aspect of the invention, polyclonal anti-EphB4 antibodies to the EphB4 peptide may be raised in avian species and the resulting polyclonal IgY antibody may be used for non-systemic prevention and/or treatment of cancers or conditions that are characterized by an upregulation of EphB4 protein. One such condition is Barrett's oesophagus as discussed herein and shown in the Examples.

The discussion above indicates that a single immunogenic peptide may be used to vaccinate the mammal or bird. It should be noted that more than one immunogenic peptide may be used. More than one immunogenic peptide may be administered concurrently or consecutively. Furthermore, the one or more immunogenic peptides may represent the same molecule or different molecules. If the one or more immunogenic peptides represent the same molecule, the different immunogenic peptides may provide a more robust immunogenic response against the one molecule or variants of the one molecule. If the one or more immunogenic peptides represent different molecules, this may provide a broader approach to inhibiting growth of target cells when the antibody-containing milk or egg product is used for preventing and/or treating a non-infectious medical condition, as described herein.

As noted above, it is also possible to employ the methods of the present invention in mammals other than bovines to produce antibody containing milk products. It may be necessary to employ these other mammals especially when bovines are incapable of mounting an effective immune response against the desired immunogen. This may occur when the sequence homology of the immunogenic peptide between bovines and the patient to be treated is high. Such other mammals as ovines, porcines and caprines may typically be employed. Since the antibody-containing milk is not intended to be used on the same scale as regular milk, the requirement for very large scale production is reduced, therefore these alternative sources of milk may be useful. It may be advantageous for reasons of heterology leading to increased immune response and/or patient preference and/or economy to produce antibody containing egg products as well or instead of antibody containing milk products.

Milk and or egg products containing antibodies to more than one specific molecule may be produced by vaccinating single mammals or birds with multiple antigens, or by mixing milk and or eggs from mammals or birds vaccinated with antigens to different target molecules.

Once an immune response has been initiated in the mammal or bird it is desirable to obtain as much antibody-containing milk or egg as possible. Typically, colostrum contains high levels of antibodies, however, as regular milk production begins, the level of antibodies generally reduces. Therefore, it may be desirable to collect only colostrum in order to obtain the antibodies. However, by the use of various vaccination methods it is possible to retain relatively high levels of antibody in the milk for extended periods of time after colostrum production has ceased. These methods are of particular use in the present invention to produce higher volumes of final product suitable for nutritional and pharmaceutical products.

In certain embodiments of the present invention, mammals, such as bovines on commercial dairy farms, may be vaccinated intramuscularly in the rump. It is envisaged that mammals will be primed prior to giving birth for maximum specific antibodies to be delivered in the colostrum, and boosted throughout lactation to maintain specific antibody levels in milk.

In the case of birds (such as chickens, geese and ducks), these can be primed at any time with booster vaccinations given at various times to maximise the antibody levels in the eggs over a long period of time.

Once an antibody-containing milk or egg product has been obtained, it will generally, although not always, be necessary to process the product into a form suitable for administration. It is important that the antibodies are not adversely affected by any of the treatments. Some of these methods require low heat in order to preserve the functionality of the antibodies. Furthermore, it is desirable that the antibodies remain protected from proteolytic actions of the animal or person to which they are to be administered.

Described herein below is an exemplary embodiment using an antibody-containing milk product. One exemplary antibody-containing milk product is bovine colostrum. The bovine colostrum retained from the first 4 days post parturition, more preferably bovine colostrum retained from the first 2 days post parturition, even more preferably bovine colostrum retained from the first day post parturition, and most preferably bovine colostrum retained from the first milking post parturition.

In particular embodiments of the present invention the antibody-containing milk product may be processed using a defatting operation. In other embodiments the process further includes an operation to remove cellular debris. In still further embodiments the process may further include an operation to remove salts, sugars, other low molecular weight entities and some water.

In particular embodiments of the present invention, the antibody-containing milk product comprises at least 4% total protein (weight %). In other embodiments the protein content may be at least 50%, or at least 70%, or at least 80%.

The antibody content of the antibody-containing milk product may also be measured. Depending on the end use of the product, IgG as a percent of the final formulation may be anything from approximately 2% of a sip feed formulation to greater than 90% for an affinity purified topical formulation.

It is envisaged that the antibody-containing milk product includes antibodies or fragments thereof as described above, such as: monoclonal or polyclonal immunoglobulins. The product may contain chimeric monoclonal antibodies or humanised monoclonal antibodies or dendrimer presented immunoactive fragments or immunoactive fragments such as F(ab) and F(ab)$_2$ fragments or recombinant immunoactive fragments, or affinity purified immunoglobulins or immunoactive fragments thereof. It will be apparent to the skilled addressee that some of the antibodies listed above may not be produced by the immunized mammal or bird and such antibodies could be added to a milk or egg product prior to administration to a patient.

It is envisaged that antibody-containing eggs produced according to the present invention can be processed using standard methods known in the art. Some of these methods require low heat in order to preserve the functionality of the antibodies. It is also envisaged that specific antibodies may be isolated from the eggs by such techniques as affinity chromatography.

The milk or egg products of the present invention may be treated by a number of methods to remove contaminating bacteria and to extend shelf life. Such methods include, but are not limited to, microfiltration.

The compositions of the invention may be administered in a range of forms such as, but not limited to, capsule, powder tablets, aerosol spray, syrup, liquid, suppository, enema or other form known in the art which is amenable to non-systemic administration. The composition may further comprise carriers or excipients suitable for gastrointestinal or other topical administration. Examples of carriers and excipients include: silica, talc, titanium dioxide, alumina, starch, kaolin, powdered cellulose, microcrystalline cellulose, Amylopectin N, sucrose, lactose, dextrose, polyvinylpyrrolidone, hydroxypropyl cellulose, methyl cellulose, hydroxyethyl cellulose, carboxymethyl cellulose, citric acid, sodium bicarbonate, magnesium stearate, shellac, cellulose acetate, cetyl alcohol, triethyl citrate, polyethylene glycol.

Preparation of a nutritional or medicament may also require formulation of the antibody-containing milk or egg product into an administrable form. For example a tablet or suppository containing the antibody-containing milk or egg product may require a coating to make it suitable for swallowing or insertion as required. Such coatings may include protective materials to prevent the enclosed product being inactivated through the stomach, for example, but allowing release of the product in the intestine of the patient. Such coatings and protective materials are known in the art.

Preparation of a nutritional product using the antibody-containing milk or egg product may also include formulation with additional nutritional components. Such additional nutritional components may have beneficial medical effects for the patient to be treated. The other components are not particularly limited, and include, for instance, amino acids, vitamins, minerals, prebiotics, probiotics and other functional ingredients.

Amino acids for inclusion in the nutritional products may be selected from the group including, but not limited to: glutamine, glutamic acid, tryptophan, alanine, arginine, aspartic acid, threonine, serine, γ-aminobutyric acid, taurine, tiotaurine, hypotaurine.

Vitamins for inclusion in the nutritional products may be selected from the group including, but not limited to: vitamin A, vitamin $B_1$, vitamin $B_2$, vitamin $B_6$, vitamin $B_{12}$, vitamin C, vitamin D, vitamin E, vitamin K, folic acid, nicotinic acid, lipoic acid, pantothenic acid, biotin, ubiquinone, prostaglandin and derivatives of these vitamins.

Minerals for inclusion in the nutritional products may be selected from the group including, but not limited to: calcium, iron, magnesium, copper, zinc, selenium and potassium.

Prebiotics for inclusion in the nutritional products may be selected from the group including, but not limited, to Fructo-oligosaccharide (FOS), Galacto-oligosaccharide (GOS), Acidic oligosaccharide (AOS) and inulin.

Other functional materials for inclusion in the nutritional products may be selected from the group including, but not limited to: St. John's wort, herbs such as Chamomile, *Gymnema*/Garcinia, plants pertaining to Chinese-style medicine such as *Eucommia ulmoides* and *Pnanx ginnseng* or extracts thereof, extracts of animal origins such as placenta, dietary fibre (such as oligosaccharides and polysaccharides), soy peptide, diet sweetener and caffeine.

The milk or egg products of the present invention may be in the form of a nutritional composition. Such compositions may contain between 10 and 60 en % lipid, between 5 and 50 en % protein, between 15 and 90 en % carbohydrate. The amounts of each component in the compositions is measured in "en %", this unit is the "energy percentage" and represents the relative amount each constituent contributes to the total caloric value of the preparation. Certain nutritional compositions may contain between 7.5 to 12.5 en % protein; 40 to 55 en % carbohydrates; and 35 to 50 en % fat.

The compositions may also contain at least one long chain polyunsaturated fatty acid (LC-PUFA) selected from the group consisting of eicosapentaenoic acid (EPA, n-3), docosahexaenoic acid (DHA, n-3) and arachidonic acid (AA, n-6), as these further reduce the respiratory tract infections and/or symptoms thereof. The present compositions may also contain AA and DHA, and optionally EPA.

The compositions may also contain at least 0.1 wt. %, at least 0.25 wt %, at least 0.5 wt. %, or at least 0.75 wt. % LC-PUFA with 20 and 22 carbon atoms of the total fat content. The content of LC-PUFA with 20 and 22 carbon atoms in the present compositions should not exceed 15 wt. % of the total fat content, optionally said content should not exceed 10 wt. %, and optionally should not exceed 5 wt. % of the total fat content.

The EPA content of the compositions should not exceed 15 wt. % of the total fat, optionally said content should not exceed 5 wt. %, and optionally should not exceed 1 wt. %. However, the EPA content may be at least 0.05 wt %, or at least 0.1 wt. % of the total fat. The DHA content should not exceed 10 wt. %, optionally said content should not exceed 5 wt. %, and optionally should not exceed 1 wt. %. However, the DHA content may be at least 0.1 wt % of the total fat. The present composition may contain at least 0.1 wt. % AA, at least 0.25 wt. % AA, or at least 0.5 wt. % AA based on total fat. The AA content should not exceed 5 wt. %, and optionally should not exceed 1 wt. % of the total fat.

Formulations known in the art that are suitable for delivery to the bladder via a catheter, to the eye via drops or ointments, oral/buccal cavity by patches or gum etc may be employed.

The milk or egg product of the present invention may also be used in the treatment and/or prevention of a skin cancer or a hyperproliferative condition of the skin. In particular embodiments of the present invention the milk or egg product may be included in a cosmetic and/or pharmaceutical topical formulation suitable for application to the skin.

It is envisaged that cosmetic formulations according to the present invention will provide a therapeutically effective dose, maintain antibody stability over time, and allow contact between antibody and target molecule. High heat is to be avoided in the formulation process in order to preserve the functionality of the antibodies. It is further envisaged that the cosmetic formulations may be in the form of creams, ointments, drops, sprays, patches, mask like formulations, and the like.

In a second aspect the present invention provides a method for preventing and/or treating a non-infectious medical condition in a patient including the step of administering in a non-systemic manner to the patient an antibody-containing milk or egg product. In one form of the invention the milk or egg product contains antibodies directed to a mammalian-derived immunogenic molecule. In other forms of the invention, the mammalian-derived immunogenic molecule may be found on the surface of a mammalian cell, such as a cancer cell. In further forms of the invention the mammalian-derived immunogenic molecule may be a mutated protein or a protein which is not normally found on the surface of a mammalian cell.

It is envisaged that the methods and products of the present invention may assist not only in the treatment of GI tract (including the oropharynx), the eye, ear, nasopharynx, bladder, vagina, uterus, cervix and skin conditions but also in their prevention. Prevention will be assisted by the fact that the antibodies only target molecules found or upregulated on cancerous cells, and by the fact that the body has barriers to systemic access of intact antibodies.

The methods of the present invention may help to prevent formation of cancer in individuals in at-risk groups. It is envisaged that antibodies within the antibody-containing milk or egg product will bind to a cell overexpressing the protein or molecule to which the antibodies are directed and subsequently result in the inhibition of growth of the cell. Accordingly, the antibody-containing milk or egg product may, for example, provide nutritional support and a preventive effect for people at risk of colorectal or other GI cancers and conditions, or it may find application in cancer-preventing cosmetics for application to the skin or other organs, or pharmaceutical formulations for application to the skin, eyes, oropharynx, uterus, vagina/cervix or bladder.

Topical treatment of corneal cancer may be the most effective means of delivering an effective treatment to the eye, which is immunologically inert and will not be adversely affected by the topical application of foreign proteins as envisaged in this application.

Current treatments for skin cancer typically involve surgery to remove the cancer. The approach of the present invention is significantly simpler than surgery to remove internal cancers. However, there is a need for prevention of skin cancer formation, a role that the milk or egg products of the present invention may be able to perform. It is envisaged that a composition incorporating a milk or egg product of the present invention may be applied safely to the skin. An antibody within the milk or egg product may bind to a cell which expresses, on its surface, a molecule associated with skin cancer. This event then leads to destruction of the cell before it can develop into a cancer. Such compositions may also find application post-surgery in reducing the likelihood of a skin cancer redeveloping.

The methods of the present invention may also find application in the treatment of a GI cancer. In one form of the invention the antibodies within the antibody-containing milk or egg product will bind to a cell overexpressing the protein to which the antibodies are directed and subsequently result in the inhibition of growth of the cell. Such an action may find use as a therapy for the GI cancer. In another form of the invention ingestion of the antibody-containing milk or egg product may be used as an additional treatment to supplement conventional treatment of the GI cancer. It is envisaged that the antibody-containing milk or egg product may increase the likelihood of, and duration of, remission of GI cancer in patients. Accordingly, the methods of the present invention may improve the survival rate per annum of GI cancer patients.

Current treatments for colorectal cancers include surgical resection with 3-5 cm disease free margins and resection of the mesentery at the origin of the blood supply, including primary lymphatic drainage sites. Aggressive treatment is required to attempt a cure of the disease. Usually colostomy can be avoided unless the cancer is within 5 cm of the anus.

Cure can be achieved with surgery alone in a large number of patients. When the cancer is detected at an early stage the cure rates are much higher. Overall, approximately 75% of patients are cured by a primary resection and of the 25% of patients who develop a recurrence, 20% of these will be cured by a second resection.

Chemotherapy is also standard for most patients. This generally includes a combination of 5-fluorouracil (5-FU) and levamisole for a duration of 1 year postoperatively and may be combined with radiation therapy. Chemotherapy with 5-FU and Levamisole has been shown to increase the overall survival in patients, over those treated by surgery alone, from 46% to 60% after 6.5 years.

Survival rates for oesophageal cancers are generally low as a result of patients frequently suffering with problems swallowing and/or eating which in turn may lead to poor nutrition. In certain embodiments of the present invention, the antibody-containing milk or egg product may be administered directly to the lumen of the GI tract in the vicinity of an oesophageal cancer. Furthermore, as discussed herein, the product may contain not only antibodies to the target cells, but also nutritional components which may assist in alleviating some of the symptoms associated with poor nutrition.

In the case of a GI condition, the methods of the present invention include the step of administering an antibody-containing milk or egg product to the patient via the lumen of the GI tract, whereby the antibodies within the milk product contact the cancer cell within the GI tract. Antibody attachment can be rapid, and long-lasting, so that even a single dose of antibody might have a significant short term effect on the condition. Continued dosing might be expected to have a significant longer term effect on the condition. Exemplary methods for administering the antibody-containing milk or egg product include, but are not limited to:

drinking the antibody-containing milk or egg product so that it passes through the GI tract whereby antibodies within the milk or egg product bind their target antigen/molecule as they pass. It is envisaged that compositions suitable for this approach may include
1) protective compounds and or
2) Concomitant antacid therapy and or
3) Viscous composition sipped over time
which will assist antibodies within the milk or egg product to survive the digestive processes within the GI tract (especially in the oesophagus), or persist in the GI tract longer to increase contact time between antibodies and target molecules.

directly introducing the antibody-containing milk or egg product into the oesophagus or intestine (large or small). This may be achieved by pouring or pumping an antibody-containing milk or egg product through a tube into the required part of the GI tract or by spraying directly onto the region requiring treatment via pump/tube sets.

for treatment of an oesophageal condition it is envisaged that a balloon positioned in or near the stomach may be used to prevent the antibody-containing milk or egg product entering the stomach too quickly, optionally an additional balloon positioned in the upper oesophagus may be used to prevent the antibody-containing milk ore egg product being regurgitated. In this way prolonged treatment of the affected or at risk area may be achieved without a large quantity of the antibody-containing milk or egg product.

for treatment of colonic conditions it is possible to introduce the antibody-containing milk product directly into the colon in the form of an enema or by colonic irrigation, or in solid or semi-solid form as a suppository.

It is envisaged that the methods and products of the present invention can reduce the incidence of GI cancer in at-risk groups, delay the onset of GI cancer in at-risk groups; and increase the remission rates, and duration of remission in GI cancer patients. As a consequence of these effects, it is hoped that there is a concomitant increase in survival rates per annum in at-risk and patient groups.

For a skin condition, the method includes the step of administering an antibody-containing milk or egg product directly to the skin of a patient, whereby antibodies within the milk or egg product contact the target cell.

It is envisaged that incorporation of the products of the present invention into cosmetics may also assist in reducing the incidence of, or preventing, skin cancer. Currently, many cosmetics include sunscreens to reduce the likelihood of sun damage to the skin. By incorporating the products of the present invention, the cosmetics could also help to undo damage already done to the skin and thereby prevent the formation of skin cancers.

For other topical applications (eyes, ears, nose, throat, vagina, cervix, bladder) direct application of a suitable pharmaceutical formulation is preferred.

Topical treatment of corneal cancer may be the most effective means of delivering an effective treatment to the eye, which is immunologically inert and will not be adversely affected by the topical application of foreign proteins as envisaged in this application.

In further aspects the present invention provides antibodies isolated from the antibody-containing milk or egg product of the present invention. Such antibodies may be isolated using standard methods known to the skilled addressee. These methods include, but are not limited to, affinity purification by binding the antibodies to immobilized antigen, by way of affinity chromatography.

The present invention also provides pharmaceutical compositions which include an antibody-containing milk or egg product of the present invention and/or an antibody of the present invention. Such compositions may also include various physiologically acceptable components making the composition suitable for administration to a patient. The various components include, but are not limited too, physiologically acceptable diluents and buffers. As discussed above, there are various routes of administration according to the present invention; the skilled addressee would be able to formulate suitable compositions for those various routes of administration.

In yet a further aspect the present invention provides a kit which may be used for diagnosing and/or treating and/or preventing a non-infectious medical condition in a patient. Such kits include an antibody-containing milk or egg product of the present invention and/or an antibody of the present invention and/or a pharmaceutical composition of the present invention. The kit may be used to diagnose and/or treat and/or prevent non-infectious medical conditions such as cancer, such as a gastrointestinal cancer or a skin cancer. In certain forms of the invention the kit may be used in the diagnosis and/or treatment and/or prevention of a gastrointestinal cancer is selected from the group consisting of: anal cancer, bile duct cancer, colorectal (colon and/or rectal) cancer, esophageal cancer, gallbladder cancer, gastric cancer, liver cancer (hepatoma), pancreatic cancer and small intestine cancer.

Specific embodiments and applications of the present invention will now be discussed in detail by reference to the accompanying examples. This discussion is in no way intended to limit the scope of the invention.

EXAMPLES

Example 1

Identification of Cell Surface Target Molecules

Samples from healthy donors and patients with oesophageal adenocarcinoma were collected at biopsy during routine endoscopy or from excess tissue remaining after oesophagectomy. Control tissue from patients was taken from an endoscopically visualised area of normal squamous epithelium, 2-5 cm proximal from the tumour margin. The tissues were immediately preserved in RNA Later™ or RNA Later Ice™. A small section of the same tissue used for RNA extraction was confirmed by a histopathologist to be normal squamous epithelium (N), or Barrett's epithelium (Intestinal Metaplasia, IM), or adenocarcinoma (Tumour, T).

RNA was extracted using Trizol™ and reverse-transcribed into cDNA using SuperScript III™. cDNA was brought to a final volume of 400 µl. 6 µl of cDNA was used in a 20 µl PCR reaction containing 1× Quantitect™ Sybr Green real-time PCR mix and 200 nM each of forward and reverse primer. PCR reactions were carried out on a Corbett Rotorgene™ real-time PCR machine (model 3000 or 6000). Gene-specific PCR signal was normalised using β-Actin. Quantification of the Ephs and Ephrins is reported relative to the colon adenocarcinoma cell line HT29, which was arbitrarily set to 1.

Data were assessed for statistical significance using the non-parametric Kruskal-Wallis test. Multiple comparisons were made by Kruskal-Wallis tests, with post hoc Bonferroni's correction. A p-value of less than 0.017 was considered significant.

Figure 2:
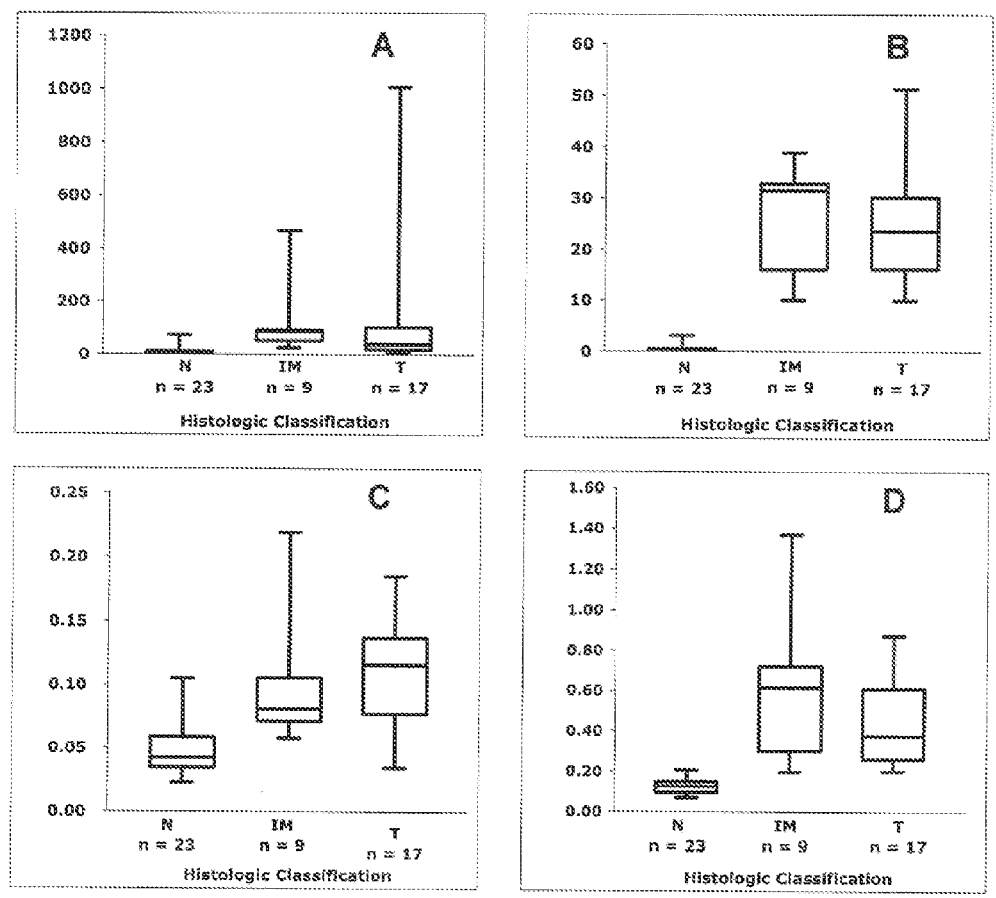
FIG. 2 shows the relative EphB1 (A), EphB2 (B), EphB4 (C) and EfnB2 (D) mRNA levels in the different histological groups. The boxes show the 25th and 75th percentile (interquartile) ranges. Median values are shown as a horizontal bar in each box. The whiskers show levels outside the 25th and 75th percentile. An asterisk (*) represents $p<0.017$ vs. normal.

There were 11 patients with oesophageal adenocarcinoma included in this study. FIGS. 1 and 2 illustrate the relative mRNA levels of Ephs and Efns in tissues from these patients and from healthy donors. Data are presented as boxplots with whiskers representing the range of data points. The three histologically-confirmed tissue types (N, IM and T) are presented in separate boxplots. All Ephs and Efns analysed showed a significant difference in mRNA levels between normal vs Barrett's tissues and normal vs oesophageal adenocarcinoma tissues.

In general, the mRNA levels of both EphA receptors assessed were significantly lower in IM and T compared to N, while the mRNA levels of all EphB receptors examined were significantly higher in IM and T compared to N. Both EfnA1 and EfnB2 mRNA levels were significantly higher in IM and T compared to N. The fold-change in median levels of mRNA for each of these genes in the different histological groups is summarised in Table 1.

TABLE 1

Fold change in median mRNA levels of Ephs and Efns in IM and T tissues relative to N tissues.

| mRNA | IM/N | T/N | approx. fold change from N |
|---|---|---|---|
| EphA1 | 0.313 | 0.236 | down 3-4x |
| EphA2 | 0.502 | 0.501 | down 2x |
| EfnA1 | 2.041 | 3.068 | up 2-3x |
| EphB1 | 20.326 | 9.093 | up 9-20x |
| EphB2 | 105.000 | 78.667 | up 80-100x |
| EphB4 | 1.929 | 2.738 | up 2-3x |
| EfnB2 | 4.769 | 2.923 | up 3-5x |

Comparing normal tissue to the IM and T groups, EphB2 mRNA levels had the highest increase in median mRNA levels (80-100 fold), and EphA1 had the greatest decrease in median mRNA levels (3-4 fold). There was trend towards a decrease in median EphB2 and EfnB2 mRNA levels in oesophageal adenocarcinoma relative to Barrett's epithelium. In contrast, there was a trend towards in increase in median EphB4 mRNA levels in oesophageal adenocarcinoma relative to Barrett's epithelium. Any of the genes showing increased expression in IM and/or T may be potential targets for raising antibodies and directing therapies, as described herein.

The significant increase in EphB4 mRNA levels in adenocarcinoma relative to normal tissue, although more modest than that of EphB2, is of interest due to the association between increased EphB4 levels and cancer cell survival. The trend towards an increase in EphB4 mRNA in oesophageal adenocarcinoma relative to Barrett's epithelium may be associated with acquisition of a transformed aggressive cancer phenotype.

Example 2

EphB4 Expression in Oesophageal Cell Lines

Figure 3:
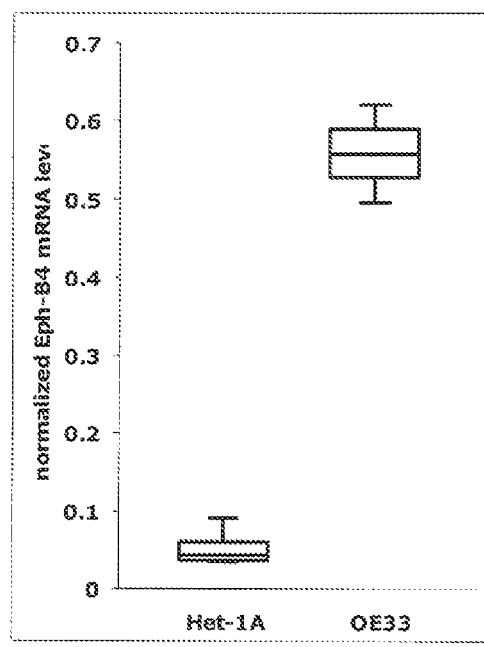
FIG. 3 shows the normalized EphB4 mRNA level in the Het1A (oesophageal epithelial cells) and OE33 (oesophageal carcinoma) cell lines.

The methods outlined in Example 1 above were used to examine EphB4 mRNA expression in Het1A and OE33 cell lines. Het-1A cells are derived from normal oesophageal epithelium and OE33 are derived from oesophageal adenocarcinoma epithelium. Four cultures of Het-1A and three cultures of OE-33 were examined. The results shown in FIG. 3 indicate that EphB4 expression is significantly higher in the adenocarcinoma-derived cell line (OE33) than in the essentially normal Het1A cell line.

Example 3

EphB4 Immunogen Preparation

Several procedures can be used to yield a suitably pure EphB4 antigen; In one process, pure ephrin B1 (or B2) ligand is used to purify EphB4 receptor by covalently attaching (ephrin-B1,B2) to a suitable chromatography matrix, and using this to affinity purify the EphB4 receptor from a crude (colon-tumor) cell extract. In another process, EphB4 receptor is purified using immuno affinity purification method, employing a specific polyclonal anti-EphB4 antibody covalently linked to a suitable chromatography matrix. In yet another process, EphB4 is produced by recombinant technology, following published procedures.

Possible methods to manufacture pure ephrin-B1(B2)-ligand include the isolation of native ephrin-B1 ligand from suitable human cells using standard biochemical protein purification techniques, such as; ion or cation exchange chromatography, size exclusion chromatography etc. A second method is to immunoaffinity purify the ephrin-B1 ligand. In both cases, final purification could be performed using a commercially produced polyclonal anti-ephrin B1 (B2) ligand antiserum. A third alternative is to manufacture recombinant ephrin-B1 ligand. This has the advantage of being able to produce large quantities of the molecule in a short time. In addition, it is only necessary to prepare the extracellular (Eph-receptor binding) portion of the molecule.

As noted above, one option for preparing the EphB4 antigen is to isolate it from a natural source, such as from various types of colon cancer cells, by an affinity purification method using the ephrin-B1 ligand prepared as above. This procedure yields a whole EphB4 receptor, with both the extracellular and intracellular portions of the molecule.

Since it is only the extracellular portion (~50 kDa of a total 120 kDa) of the molecule that is relevant as the antigen, an alternative approach to preparing the EphB4 molecule is to use recombinant methodology to prepare only the extracellular domain. Recombinant methodology has the advantage of permitting large scale preparation of a specific molecule. A potential drawback however, is that post-translational modifications are not generally reproduced in recombinantly produced molecules. If a modified residue in the extracellular domain is important for eliciting an immune reaction to EphB4 purified protein may be the better approach.

It is possible to use several insolubilised proteolytic enzymes to systematically degrade (hydrolyze) the EphB4-receptor. The enzymes used include; trypsin, pepsin, papain, and bromelin. The proteolytic enzyme hydrolysis of EphB4 receptor yields various peptides, from both the intra and extracellular portions of the molecule. These peptides are purified to yield individual EphB4 peptides. Since size exclusion chromatography separates the peptides only on size difference, different peptides that have the same size are eluted in the same fraction. However if it is found that these peptides are good antigens, they can be further separated by ion-exchange (or other) chromatography.

By using the insolubilised proteolytic enzymes (trypsin, pepsin etc.) limited hydrolysis of EphB4 can be performed. This yields a few large EphB4 protein fragments (20 to 40 kDa size). These protein fragments are large enough to elicit a good antibody response in the immunized animals. These large protein fragments also retain the regional protein surface topography (tertiary-structure). This may ensure that the antibodies produced will be against epitopes that are present on the native EphB4 protein.

Example 4

EphB4 Antigen Identification

It is necessary to establish which of the EphB4 peptide fragments, when used as antigens, generate high affinity EphB4 antibodies. To achieve this, several rabbits (for example) can be immunized with the above peptides, and the resultant antiserum tested in an in vitro cell culture assay, using human colon cancer cell lines.

As mentioned above, only the peptide fragments derived from the extracellular portion of the EphB4 receptor could be used as effective antigens. It is only this portion of the molecule that is accessible to antibodies outside a cell, also the ephrin ligand binding site is on this part of the molecule, and blocking it, stops EphB4 signaling.

Rabbits can be immunized with the whole (undigested) EphB4-receptor. The antiserum from these rabbits would serve as a "Control-serum" against which the other antisera would be tested. Rabbits can also be immunized with the EphB4 peptide fragments (every animal in this group would be immunized with the mixture containing all of the peptide fragments).

For immunizing, animals other than rabbits could be used; for example mice, rats, guinea pigs etc. However small animals are difficult to immunize and bleed, and the amount of anti-serum that could be collected is very limited.

While it would be possible to immunize rabbits with individual peptide fragments, and obtain antiserum specific to each particular EphB4 peptide only, a large amount of work would be involved in preparing pure fragments and immunizing several animals per fragment. Immunization with the mixture of fragments is more efficient. After approximately 12 weeks the crude rabbit antisera can be tested for efficacy in an in vitro cell culture assay using human colon tumor cells. These assays only need to demonstrate some inhibition in tumor cell growth and proliferation. Once a positive anti-tumor effect is demonstrated, the anti-EphB4 antibodies are purified from the hyperimmune rabbit serum, and the most effective antibodies are identified. This is done by preparing small affinity columns for each of the individual EphB4 peptide fragments that were used as antigens. The crude rabbit serum is passed through the columns, were the appropriate antibodies bind to their respective peptide antigens. In this manner all the anti-EphB4 (peptide fragment) antibodies are separated out from the crude rabbit serum. The specific EphB4 peptide antibodies are then tested (individually) in the in vitro cell culture assay using human colon cancer cell lines. In this way the EphB4 peptide fragments that are the most effective antigens can be identified. These peptides are then used as the immunogen (vaccinating antigen) to generate the anti-EphB4 antibody-containing milk product.

Although it would be possible to use a commercially available α-EphB4 polyclonal antibody to identify EphB4 protein fragments that are immunogenic, the problem with this procedure is, that this antibody might not react well with abnormal/tumour-derived EphB4 receptors. It is these, cancer/tumour-derived, abnormal (mutated), EphB4-receptors that are most important as antigens. Using commercial antibodies it is possible that biologically significant antigens might be overlooked.

The amino acid sequence of these fragments can be determined, and from this a method to manufacture them by recombinant means, can be established. This allows for unlimited amounts of antigen to be manufactured. The antigen would yield effective anti-EphB4 antibodies of high affinity.

Future patent applications may be filed in Australia or overseas on the basis of the present application, for example by claiming priority from the present application, by claiming a divisional status and/or by claiming a continuation status. It is to be understood that the following claims are provided by way of example only, and are not intended to limit the scope of what may be claimed in any such future application; nor should the claims be considered to limit the understanding of (or exclude other understandings of) the invention or inventions inherent in the present disclosure. Features may be added to or omitted from the example claims at a later date, so as to further define the invention or inventions.

Example 5

Peptide Manufacture and Conjugation

Synthesis of peptides for use in the methods of the present invention can be performed by standard methods know to those skilled in the art. In effect, amino acid residues are sequentially added to an immobilized amino acid by an automated process. Once an amino acid has been added it is then de-protected in order for it to receive the next amino acid residue. The amino acid residues are protected to ensure that only a single residue is added per reaction step and that side chains of the amino acid residues do not undergo reactions. Synthesis of peptides can generally be performed according to the following process:

Carrier resin Fmoc-NH is placed into a reaction container of automatic synthesizer. DMF is added thereto, and stirred for 3 minutes. The solution is then drained. A 30% piperidine-DMF solution is then added, the mixture is stirred for 4 minutes, the solution is drained, and this operation is repeated.

The carrier resin is then washed with DMF for 1 minute, the solution is drained, and this operation is repeated 5 times. Protected amino acid residues are then added sequentially with intervening partial deprotection steps to allow addition of residues in the correct position and in the correct sequence.

The peptides can then be cleaved from the resin together with the removal of the side-chain protecting groups. This crude product is then dissolved in aqueous acetic acid solution, and then passed through a cartridge filled with reversephase silica gel to adhere the peptides. Upon washing with an aqueous solution of 0.1% TFA and 15% acetonitrile and eluting with an aqueous solution of 0.1% TFA and 25% acetonitrile, a fraction containing the peptide is obtained.

The peptide is generally synthesised with a terminal cysteine residue which allows the peptide to then be conjugated with KLH to raise immunogenicity of the peptide. For example a 10 mg/ml KLH solution is prepared by dissolving KLH in PBS, and 1/10 the volume of 25 mg/ml MBS (N-(m-Maleimidobenzoyloxy)succinimide) is added drop wise, and then allowed to react while stirring for 30 minutes. Next, 2.5 mg of KLH-MB, which is obtained by removing free MBS using Sephadex G-25 column pre-equilibrated in PBS, is mixed with 1 mg of the peptide dissolved in 0.1 M sodium phosphate buffer (pH 7.0). These are allowed to react while stirring for 3 hours at room temperature. After the reaction, the product is dialyzed with PBS, and can used as the immunogen.

Example 6

Maintenance of Antibody Activity During Acid/Pepsin Treatment

To investigate the protective effect of bovine colostrum as a protectant of antibody activity in a gastric environment a simulated gastric fluid was tested on a specific monoclonal antibody. Activity was compared in the presence and absence of bovine colostrum.

A virus-specific IgG2a monoclonal, diluted 1:10 in phosphate buffered saline, was sued in this example. The simulated gastric fluid was a 0.32% solution of porcine pepsin in 0.03M NaCl and adjusted to pH 1.2 with HCl. Defatted, freeze dried Bovine Colostrum was sourced from non-immunised cows and reconstituted at 300 mg/mL in water.

Aliquots of antibody, diluted 1:10 in phosphate buffered saline, were mixed with an equal volume of either the reconstituted colostrum or water. A mixture of the colostrum preparation and water was used as a control. The mixtures were preheated in a 37° C. water bath for 5 minutes before assaying antibody activity.

Treatment of the monoclonal antibody with simulated gastric fluid resulted in a 6-fold reduction in the activity of the antibody. In contrast, the addition of colostrum to the antibody preparation provided protection of the antibody from the effect of the pepsin and acid. In the presence of colostrum, the protected antibody showed no reduction of activity. Using this antibody model, bovine colostrum has been shown to provide protection of antibody activity in a simulated gastric environment.

Example 7

Use of Antibody-Containing Milk Product

A patient presents with an unknown oesophageal condition. A biopsy of oesophagus is taken and the expression level of EphB4 is determined and found to be higher than in the surrounding normal oesophageal tissue. It is concluded that the patient is suffering Barrett's oesophagus. The patient is administered (orally) daily doses of a milk product containing antibodies directed to EphB4. Continued administration of the milk product has a therapeutic effect and the patient's symptoms of Barrett's oesophagus are alleviated.

Example 8

Raising Antibodies in Chickens

Having identified a potential target molecule and epitope thereof, an amount of antigen sufficient to immunize up to 10 adult female chickens is prepared. Amounts of peptide are known to those of skill in the art and can be readily optimised with minimal experimentation.

The dilute antigen mixture is injected into each chicken and repeated immunizations are given at two-week intervals over a six-month period of time. Eggs were collected from chickens beginning one month after the first immunization.

Example 9

Use of Antibody-Containing Egg Product

It has previously been shown that antibodies in eggs, or fractions thereof, produced in female avians hyperimmunized with specific bacterial antigens, survive into the gut and remain active. Accordingly, if a patient presents with Barrett's oesophagus, as in Example 5, the patient may be administered (orally) daily doses of an egg product containing antibodies directed to EphB4. The egg product may be in the form of an "egg-flip" a day. The egg flip could be made using spray dried egg yolk as an ingredient. Continued administration of the egg product then has a therapeutic effect and the patient's symptoms of Barrett's oesophagus are alleviated. Such a protocol could also be employed in the treatment and/or prevention of cancer of the GI tract.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention claimed is:

1. A method for treating Barrett's oesophagus in a mammal, including a human exhibiting Barrett's oesophagus, comprising topically administering a therapeutically effective amount of a milk or egg product comprising an antibody and antibody binding portions thereof, or a combination of antibodies and antibody binding portions thereof directed against the extracellular domain of EphB4, wherein the milk or egg product comprising an antibody is obtained by vaccinating a mammal or a bird with EphB4 or antigenic portions thereof.

2. The method of claim 1, wherein the administration comprises introducing the therapeutically effective amount of a milk or egg product comprising an antibody directly into the gastrointestinal tract of the mammal.

3. The method of claim 1, wherein the effective amount of the milk or egg product comprising an antibody is administered orally.

4. The method of claim 1, wherein the antibody directed against the extracellular domain of EphB4 is raised against a peptide comprising the sequence PVAGSCVVDAVPAPGPSPSLY, as set forth in SEQ ID NO:4.

* * * * *

UNITED STATES PATENT AND TRADEMARK OFFICE
CERTIFICATE OF CORRECTION

| | |
|---|---|
| PATENT NO. | : 8,834,872 B2 |
| APPLICATION NO. | : 13/927491 |
| DATED | : September 16, 2014 |
| INVENTOR(S) | : Antony William Scammell |

Page 1 of 1

It is certified that error appears in the above-identified patent and that said Letters Patent is hereby corrected as shown below:

Title Page, References cited Foreign Patent Documents: "1303889" should be --1303869--.

Signed and Sealed this
Thirtieth Day of December, 2014

Michelle K. Lee
*Deputy Director of the United States Patent and Trademark Office*

SEQUENCE LISTING

```
<160> NUMBER OF SEQ ID NOS: 5

<210> SEQ ID NO 1
<211> LENGTH: 987
<212> TYPE: PRT
<213> ORGANISM: Homo sapiens

<400> SEQUENCE: 1

Met Glu Leu Arg Val Leu Leu Cys Trp Ala Ser Leu Ala Ala Ala Leu
1               5                   10                  15
```

```
Glu Glu Thr Leu Leu Asn Thr Lys Leu Glu Thr Ala Asp Leu Lys Trp
             20                  25                  30
Val Thr Phe Pro Gln Val Asp Gly Gln Trp Glu Glu Leu Ser Gly Leu
         35                  40                  45
Asp Glu Glu Gln His Ser Val Arg Thr Tyr Glu Val Cys Asp Val Gln
     50                  55                  60
Arg Ala Pro Gly Gln Ala His Trp Leu Arg Thr Gly Trp Val Pro Arg
 65                  70                  75                  80
Arg Gly Ala Val His Val Tyr Ala Thr Leu Arg Phe Thr Met Leu Glu
                 85                  90                  95
Cys Leu Ser Leu Pro Arg Ala Gly Arg Ser Cys Lys Glu Thr Phe Thr
            100                 105                 110
Val Phe Tyr Tyr Glu Ser Asp Ala Asp Thr Ala Thr Ala Leu Thr Pro
        115                 120                 125
Ala Trp Met Glu Asn Pro Tyr Ile Lys Val Asp Thr Val Ala Ala Glu
    130                 135                 140
His Leu Thr Arg Lys Arg Pro Gly Ala Glu Ala Thr Gly Lys Val Asn
145                 150                 155                 160
Val Arg Thr Leu Arg Leu Gly Pro Leu Ser Lys Ala Gly Phe Tyr Leu
                165                 170                 175
Ala Phe Gln Asp Gln Gly Ala Cys Met Ala Leu Leu Ser Leu His Leu
            180                 185                 190
Phe Tyr Lys Lys Cys Ala Gln Leu Thr Val Asn Leu Thr Arg Phe Pro
        195                 200                 205
Glu Thr Val Pro Arg Glu Leu Val Val Pro Val Ala Gly Ser Cys Val
    210                 215                 220
Val Asp Ala Val Pro Ala Pro Gly Pro Ser Pro Ser Leu Tyr Cys Arg
225                 230                 235                 240
Glu Asp Gly Gln Trp Ala Glu Gln Pro Val Thr Gly Cys Ser Cys Ala
                245                 250                 255
Pro Gly Phe Glu Ala Ala Glu Gly Asn Thr Lys Cys Arg Ala Cys Ala
            260                 265                 270
Gln Gly Thr Phe Lys Pro Leu Ser Gly Glu Gly Ser Cys Gln Pro Cys
        275                 280                 285
Pro Ala Asn Ser His Ser Asn Thr Ile Gly Ser Ala Val Cys Gln Cys
    290                 295                 300
Arg Val Gly Tyr Phe Arg Ala Arg Thr Asp Pro Arg Gly Ala Pro Cys
305                 310                 315                 320
Thr Thr Pro Pro Ser Ala Pro Arg Ser Val Val Ser Arg Leu Asn Gly
                325                 330                 335
Ser Ser Leu His Leu Glu Trp Ser Ala Pro Leu Glu Ser Gly Gly Arg
            340                 345                 350
Glu Asp Leu Thr Tyr Ala Leu Arg Cys Arg Glu Cys Arg Pro Gly Gly
        355                 360                 365
Ser Cys Ala Pro Cys Gly Gly Asp Leu Thr Phe Asp Pro Gly Pro Arg
    370                 375                 380
Asp Leu Val Glu Pro Trp Val Val Arg Gly Leu Arg Pro Asp Phe
385                 390                 395                 400
Thr Tyr Thr Phe Glu Val Thr Ala Leu Asn Gly Val Ser Ser Leu Ala
                405                 410                 415
Thr Gly Pro Val Pro Phe Glu Pro Val Asn Val Thr Thr Asp Arg Glu
            420                 425                 430
Val Pro Pro Ala Val Ser Asp Ile Arg Val Thr Arg Ser Ser Pro Ser
```

```
                 435                 440                 445
Ser Leu Ser Leu Ala Trp Ala Val Pro Arg Ala Pro Ser Gly Ala Val
450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
                500                 505                 510

Ala Gly Tyr Gly Pro Phe Gly Gln Glu His His Ser Gln Thr Gln Leu
                515                 520                 525

Asp Glu Ser Glu Gly Trp Arg Glu Gln Leu Ala Leu Ile Ala Gly Thr
                530                 535                 540

Ala Val Val Gly Val Val Leu Val Leu Val Val Ile Val Val Ala Val
545                 550                 555                 560

Leu Cys Leu Arg Lys Gln Ser Asn Gly Arg Glu Ala Glu Tyr Ser Asp
                565                 570                 575

Lys His Gly Gln Tyr Leu Ile Gly His Gly Thr Lys Val Tyr Ile Asp
                580                 585                 590

Pro Phe Thr Tyr Glu Asp Pro Asn Glu Ala Val Arg Glu Phe Ala Lys
                595                 600                 605

Glu Ile Asp Val Ser Tyr Val Lys Ile Glu Glu Val Ile Gly Ala Gly
                610                 615                 620

Glu Phe Gly Glu Val Cys Arg Gly Arg Leu Lys Ala Pro Gly Lys Lys
625                 630                 635                 640

Glu Ser Cys Val Ala Ile Lys Thr Leu Lys Gly Gly Tyr Thr Glu Arg
                645                 650                 655

Gln Arg Arg Glu Phe Leu Ser Glu Ala Ser Ile Met Gly Gln Phe Glu
                660                 665                 670

His Pro Asn Ile Ile Arg Leu Glu Gly Val Val Thr Asn Ser Met Pro
                675                 680                 685

Val Met Ile Leu Thr Glu Phe Met Glu Asn Gly Ala Leu Asp Ser Phe
690                 695                 700

Leu Arg Leu Asn Asp Gly Gln Phe Thr Val Ile Gln Leu Val Gly Met
705                 710                 715                 720

Leu Arg Gly Ile Ala Ser Gly Met Arg Tyr Leu Ala Glu Met Ser Tyr
                725                 730                 735

Val His Arg Asp Leu Ala Ala Arg Asn Ile Leu Val Asn Ser Asn Leu
                740                 745                 750

Val Cys Lys Val Ser Asp Phe Gly Leu Ser Arg Phe Leu Glu Glu Asn
                755                 760                 765

Ser Ser Asp Pro Thr Tyr Thr Ser Ser Leu Gly Gly Lys Ile Pro Ile
                770                 775                 780

Arg Trp Thr Ala Pro Glu Ala Ile Ala Phe Arg Lys Phe Thr Ser Ala
785                 790                 795                 800

Ser Asp Ala Trp Ser Tyr Gly Ile Val Met Trp Glu Val Met Ser Phe
                805                 810                 815

Gly Glu Arg Pro Tyr Trp Asp Met Ser Asn Gln Asp Val Ile Asn Ala
                820                 825                 830

Ile Glu Gln Asp Tyr Arg Leu Pro Pro Pro Asp Cys Pro Thr Ser
                835                 840                 845

Leu His Gln Leu Met Leu Asp Cys Trp Gln Lys Asp Arg Asn Ala Arg
850                 855                 860
```

Pro Arg Phe Pro Gln Val Val Ser Ala Leu Asp Lys Met Ile Arg Asn
865                 870                 875                 880

Pro Ala Ser Leu Lys Ile Val Ala Arg Glu Asn Gly Gly Ala Ser His
            885                 890                 895

Pro Leu Leu Asp Gln Arg Gln Pro His Tyr Ser Ala Phe Gly Ser Val
        900                 905                 910

Gly Glu Trp Leu Arg Ala Ile Lys Met Gly Arg Tyr Glu Glu Ser Phe
            915                 920                 925

Ala Ala Ala Gly Phe Gly Ser Phe Glu Leu Val Ser Gln Ile Ser Ala
930                 935                 940

Glu Asp Leu Leu Arg Ile Gly Val Thr Leu Ala Gly His Gln Lys Lys
945                 950                 955                 960

Ile Leu Ala Ser Val Gln His Met Lys Ser Gln Ala Lys Pro Gly Thr
            965                 970                 975

Pro Gly Gly Thr Gly Gly Pro Ala Pro Gln Tyr
        980                 985

<210> SEQ ID NO 2
<211> LENGTH: 987
<212> TYPE: PRT
<213> ORGANISM: Mus musculus

<400> SEQUENCE: 2

Met Glu Leu Arg Ala Leu Leu Cys Trp Ala Ser Leu Ala Thr Ala Leu
1               5                   10                  15

Glu Glu Thr Leu Leu Asn Thr Lys Leu Glu Thr Ala Asp Leu Lys Trp
            20                  25                  30

Val Thr Tyr Pro Gln Ala Glu Gly Gln Trp Glu Glu Leu Ser Gly Leu
        35                  40                  45

Asp Glu Glu Gln His Ser Val Arg Thr Tyr Glu Val Cys Asp Met Lys
    50                  55                  60

Arg Pro Gly Gly Gln Ala His Trp Leu Arg Thr Gly Trp Val Pro Arg
65                  70                  75                  80

Arg Gly Ala Val His Val Tyr Ala Thr Ile Arg Phe Thr Met Met Glu
                85                  90                  95

Cys Leu Ser Leu Pro Arg Ala Ser Arg Ser Cys Lys Glu Thr Phe Thr
            100                 105                 110

Val Phe Tyr Tyr Glu Ser Glu Ala Asp Thr Ala Thr Ala His Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Ile Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ser Trp Leu Ile Thr Asn Leu Thr Tyr Phe Pro
        195                 200                 205

Glu Thr Val Pro Arg Glu Leu Val Val Pro Val Ala Gly Ser Cys Val
    210                 215                 220

Ala Asn Ala Val Pro Thr Ala Asn Pro Ser Pro Ser Leu Tyr Cys Arg
225                 230                 235                 240

Glu Asp Gly Gln Trp Ala Glu Gln Gln Val Thr Gly Cys Ser Cys Ala

```
              245                 250                 255
Pro Gly Tyr Glu Ala Ala Glu Ser Asn Lys Val Cys Arg Ala Cys Gly
            260                 265                 270
Gln Gly Thr Phe Lys Pro Gln Ile Gly Asp Glu Ser Cys Leu Pro Cys
            275                 280                 285
Pro Ala Asn Ser His Ser Asn Asn Ile Gly Ser Pro Val Cys Leu Cys
290                 295                 300
Arg Ile Gly Tyr Tyr Arg Ala Arg Ser Asp Pro Arg Ser Ser Pro Cys
305                 310                 315                 320
Thr Thr Pro Pro Ser Ala Pro Arg Ser Val Val His His Leu Asn Gly
                325                 330                 335
Ser Thr Leu Arg Leu Glu Trp Ser Ala Pro Leu Glu Ser Gly Gly Arg
            340                 345                 350
Glu Asp Leu Thr Tyr Ala Val Arg Cys Arg Glu Cys Arg Pro Gly Gly
            355                 360                 365
Ser Cys Leu Pro Cys Gly Gly Asp Met Thr Phe Asp Pro Gly Pro Arg
            370                 375                 380
Asp Leu Val Glu Pro Trp Val Ala Ile Arg Gly Leu Arg Pro Asp Val
385                 390                 395                 400
Thr Tyr Thr Phe Glu Val Ala Ala Leu Asn Gly Val Ser Thr Leu Ala
                405                 410                 415
Thr Gly Pro Pro Phe Glu Pro Val Asn Val Thr Thr Asp Arg Glu
            420                 425                 430
Val Pro Pro Ala Val Ser Asp Ile Arg Val Thr Arg Ser Ser Pro Ser
            435                 440                 445
Ser Leu Ile Leu Ser Trp Ala Leu Pro Arg Ala Pro Ser Gly Ala Val
450                 455                 460
Leu Asp Tyr Glu Val Lys Tyr His Glu Lys Gly Ala Glu Gly Pro Ser
465                 470                 475                 480
Ser Val Arg Phe Leu Lys Thr Ser Glu Asn Arg Ala Glu Leu Arg Gly
                485                 490                 495
Leu Lys Arg Gly Ala Ser Tyr Leu Val Pro Val Arg Ala Arg Ser Glu
            500                 505                 510
Ala Gly Tyr Gly Pro Phe Gly Gln Glu His His Ser Gln Thr Gln Leu
            515                 520                 525
Asp Glu Ser Glu Ser Trp Arg Glu Gln Leu Ala Leu Ile Ala Gly Thr
530                 535                 540
Ala Val Val Gly Val Val Leu Val Leu Val Val Ile Ile Ala Val
545                 550                 555                 560
Leu Cys Phe Arg Lys Gln Ser Tyr Gly Arg Glu Val Glu Tyr Ser Asp
                565                 570                 575
Lys His Gly Gln Tyr Leu Ile Gly His Gly Thr Lys Val Tyr Ile Asp
            580                 585                 590
Pro Phe Thr Tyr Glu Asp Pro Asn Glu Ala Val Arg Glu Phe Ala Lys
            595                 600                 605
Glu Ile Asp Val Ser Tyr Val Lys Ile Glu Glu Val Ile Gly Ala Gly
610                 615                 620
Glu Phe Gly Glu Val Cys Arg Gly Arg Leu Lys Ala Pro Gly Lys Lys
625                 630                 635                 640
Glu Ser Cys Val Ala Ile Lys Thr Leu Lys Gly Gly Tyr Thr Glu Arg
                645                 650                 655
Gln Arg Arg Glu Phe Leu Ser Glu Ala Ser Ile Met Gly Gln Phe Glu
            660                 665                 670
```

-continued

```
His Pro Asn Ile Ile Arg Leu Glu Gly Val Val Thr Asn Ser Val Pro
        675                 680                 685

Val Met Ile Leu Thr Glu Phe Met Glu Asn Gly Ala Leu Asp Ser Phe
690                 695                 700

Leu Arg Leu Asn Asp Gly Gln Phe Thr Val Ile Gln Leu Val Gly Met
705                 710                 715                 720

Leu Arg Gly Ile Ala Ser Gly Met Arg Tyr Leu Ala Glu Met Ser Tyr
                725                 730                 735

Val His Arg Asp Leu Ala Ala Arg Asn Ile Leu Val Asn Ser Asn Leu
            740                 745                 750

Val Cys Lys Val Ser Asp Phe Gly Leu Ser Arg Phe Leu Glu Glu Asn
        755                 760                 765

Ser Ser Asp Pro Thr Tyr Thr Ser Ser Leu Gly Gly Lys Ile Pro Ile
    770                 775                 780

Arg Trp Thr Ala Pro Glu Ala Ile Ala Phe Arg Lys Phe Thr Ser Ala
785                 790                 795                 800

Ser Asp Ala Trp Ser Tyr Gly Ile Val Met Trp Glu Val Met Ser Phe
                805                 810                 815

Gly Glu Arg Pro Tyr Trp Asp Met Ser Asn Gln Asp Val Ile Asn Ala
            820                 825                 830

Ile Glu Gln Asp Tyr Arg Leu Pro Pro Pro Asp Cys Pro Thr Ser
        835                 840                 845

Leu His Gln Leu Met Leu Asp Cys Trp Gln Lys Asp Arg Asn Ala Arg
    850                 855                 860

Pro Arg Phe Pro Gln Val Ser Ala Leu Asp Lys Met Ile Arg Asn
865                 870                 875                 880

Pro Ala Ser Leu Lys Ile Val Ala Arg Glu Asn Gly Gly Ala Ser His
                885                 890                 895

Pro Leu Leu Asp Gln Arg Gln Pro His Tyr Ser Ala Phe Gly Ser Val
            900                 905                 910

Gly Glu Trp Leu Arg Ala Ile Lys Met Gly Arg Tyr Glu Glu Ser Phe
        915                 920                 925

Ala Ala Ala Gly Phe Gly Ser Phe Glu Val Val Ser Gln Ile Ser Ala
    930                 935                 940

Glu Asp Leu Leu Arg Ile Gly Val Thr Leu Ala Gly His Gln Lys Lys
945                 950                 955                 960

Ile Leu Ala Ser Val Gln His Met Lys Ser Gln Ala Lys Pro Gly Ala
                965                 970                 975

Pro Gly Gly Thr Gly Gly Pro Ala Gln Gln Phe
            980                 985
```

<210> SEQ ID NO 3
<211> LENGTH: 987
<212> TYPE: PRT
<213> ORGANISM: Bos taurus

<400> SEQUENCE: 3

```
Met Glu Leu Arg Ala Leu Leu Cys Trp Ala Ser Leu Ala Ala Ala Leu
1               5                   10                  15

Glu Glu Thr Leu Leu Asn Thr Lys Leu Glu Thr Ala Asp Leu Lys Trp
                20                  25                  30

Val Thr Phe Pro Gln Ala Asp Gly Gln Trp Glu Glu Leu Ser Gly Leu
            35                  40                  45

Asp Glu Glu Gln His Ser Val Arg Thr Tyr Glu Val Cys Asp Met Gln
```

-continued

```
                50                  55                  60
Arg Ala Pro Gly Leu Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
                100                 105                 110

Val Phe Tyr Phe Glu Ser Asp Ala Asp Thr Ala Thr Ala His Thr Pro
                115                 120                 125

Ala Trp Met Glu Asn Pro Tyr Ile Lys Val Asp Thr Val Ala Ala Glu
                130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Thr Lys Ala Gly Phe Tyr Leu
                165                 170                 175

Ala Phe Gln Asp Gln Gly Ala Cys Met Ala Leu Leu Ser Leu His Leu
                180                 185                 190

Phe Tyr Lys Lys Cys Ala Gln Gln Thr Val Asn Leu Thr Tyr Phe Pro
                195                 200                 205

Glu Thr Val Pro Arg Glu Leu Val Val Pro Val Ala Gly Ser Cys Val
                210                 215                 220

Ala Asp Ala Met Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Asn
                245                 250                 255

Ala Gly Phe Glu Ala Ala Glu Gly Asn Thr Lys Cys Arg Ala Cys Ala
                260                 265                 270

Gln Gly Thr Phe Lys Pro Leu Ser Gly Glu Gly Ser Cys Gln Pro Cys
                275                 280                 285

Pro Ala Asn Ser His Ser Asn Ala Ile Gly Ser Ser Ile Cys Gln Cys
                290                 295                 300

Arg Ile Gly Tyr Phe Arg Ala Ser Thr Asp Pro Arg Ser Ala Pro Cys
305                 310                 315                 320

Thr Thr Pro Pro Ser Ala Pro Arg Ser Val Val Pro Arg Leu Asn Gly
                325                 330                 335

Ser Ala Leu Arg Leu Glu Trp Ser Ala Pro Leu Glu Ser Gly Gly Arg
                340                 345                 350

Glu Asp Leu Thr Tyr Ala Leu Arg Cys Arg Glu Cys Arg Pro Gly Gly
                355                 360                 365

Ser Cys Thr Pro Cys Gly Gly Asp Leu Thr Phe Asp Pro Gly Pro Arg
370                 375                 380

Asp Leu Val Glu Pro Trp Val Ala Ile Arg Gly Leu Arg Pro Asp Val
385                 390                 395                 400

Thr Tyr Thr Phe Glu Val Thr Ala Leu Asn Gly Val Ser Ser Leu Ala
                405                 410                 415

Ser Gly Pro Val Pro Phe Glu Ala Val Asn Val Thr Thr Asp Arg Glu
                420                 425                 430

Val Pro Pro Pro Val Ser Asp Ile Arg Val Thr Arg Ser Ser Pro Ser
                435                 440                 445

Ser Leu Ser Leu Ala Trp Ala Val Pro Arg Ala Pro Ser Gly Ala Val
                450                 455                 460

Leu Asp Tyr Glu Val Lys Tyr His Glu Lys Gly Ala Glu Gly Pro Ser
465                 470                 475                 480
```

```
Ser Val Arg Phe Leu Lys Thr Ser Glu Asn Arg Ala Glu Leu Arg Gly
            485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
            515                 520                 525

Asp Glu Asn Glu Thr Trp Arg Glu Gln Leu Ala Leu Ile Ala Gly Thr
            530                 535                 540

Ala Ala Val Gly Val Val Leu Val Leu Val Val Ile Val Ile Ala Val
545                 550                 555                 560

Leu Cys Leu Arg Lys Gln Ser Asn Gly Arg Glu Ala Glu Tyr Ser Asp
            565                 570                 575

Lys His Ala Gln Tyr Leu Ile Gly His Gly Thr Lys Val Tyr Ile Asp
            580                 585                 590

Pro Phe Thr Tyr Glu Asp Pro Asn Glu Ala Val Arg Glu Phe Ala Lys
            595                 600                 605

Glu Ile Asp Val Ser Tyr Val Lys Ile Glu Glu Val Ile Gly Ala Gly
            610                 615                 620

Glu Phe Gly Glu Val Cys Arg Gly Arg Leu Lys Ala Pro Gly Lys Lys
625                 630                 635                 640

Glu Ser Cys Val Ala Ile Lys Thr Leu Lys Gly Gly Tyr Thr Glu Arg
            645                 650                 655

Gln Arg Arg Glu Phe Leu Ser Glu Ala Ser Ile Met Gly Gln Phe Glu
            660                 665                 670

His Pro Asn Ile Ile Arg Leu Glu Gly Val Val Thr Asn Ser Val Pro
            675                 680                 685

Val Met Ile Leu Thr Glu Phe Met Glu Asn Gly Ala Leu Asp Ser Phe
690                 695                 700

Leu Arg Leu Asn Asp Gly Gln Phe Thr Val Ile Gln Leu Val Gly Met
705                 710                 715                 720

Leu Arg Gly Ile Ala Ser Gly Met Arg Tyr Leu Ala Glu Met Ser Tyr
            725                 730                 735

Val His Arg Asp Leu Ala Ala Arg Asn Ile Leu Val Asn Ser Asn Leu
            740                 745                 750

Val Cys Lys Val Ser Asp Phe Gly Leu Ser Arg Phe Leu Glu Glu Asn
            755                 760                 765

Ser Ser Asp Pro Thr Tyr Thr Ser Ser Leu Gly Gly Lys Ile Pro Ile
            770                 775                 780

Arg Trp Thr Ala Pro Glu Ala Ile Ala Phe Arg Lys Phe Thr Ser Ala
785                 790                 795                 800

Ser Asp Ala Trp Ser Tyr Gly Ile Val Met Trp Glu Val Met Ser Phe
            805                 810                 815

Gly Glu Arg Pro Tyr Trp Asp Met Ser Asn Gln Asp Val Ile Asn Ala
            820                 825                 830

Ile Glu Gln Asp Tyr Arg Leu Pro Pro Pro Asp Cys Pro Thr Ser
            835                 840                 845

Leu His Gln Leu Met Leu Asp Cys Trp Gln Lys Asp Arg Asn Ala Arg
            850                 855                 860

Pro Arg Phe Pro Gln Val Val Ser Ala Leu Asp Lys Met Ile Arg Asn
865                 870                 875                 880

Pro Ala Ser Leu Lys Ile Val Ala Arg Glu Asn Gly Gly Ala Ser His
            885                 890                 895
```

```
Pro Leu Leu Asp Gln Arg Gln Pro His Tyr Ser Ala Phe Gly Ser Val
            900                 905                 910

Gly Glu Trp Leu Arg Ala Ile Lys Met Gly Arg Tyr Glu Glu Ser Phe
        915                 920                 925

Ala Ala Ala Gly Phe Gly Ser Phe Glu Leu Val Ser Gln Ile Ser Thr
    930                 935                 940

Glu Asp Leu Leu Arg Ile Gly Val Thr Leu Ala Gly His Gln Lys Lys
945                 950                 955                 960

Ile Leu Ala Ser Val Gln His Met Lys Ser Gln Ala Lys Pro Gly Ala
                965                 970                 975

Pro Gly Gly Ser Gly Ala Pro Ala Pro Gln Tyr
            980                 985

<210> SEQ ID NO 4
<211> LENGTH: 21
<212> TYPE: PRT
<213> ORGANISM: Homo sapiens

<400> SEQUENCE: 4

Pro Val Ala Gly Ser Cys Val Val Asp Ala Val Pro Ala Pro Gly Pro
1               5                   10                  15

Ser Pro Ser Leu Tyr
            20

<210> SEQ ID NO 5
<211> LENGTH: 21
<212> TYPE: PRT
<213> ORGANISM: Bos taurus

<400> SEQUENCE: 5

Pro Val Ala Gly Ser Cys Val Ala Asp Ala Met Pro Ala Pro Gly Pro
1               5                   10                  15

Ser Pro Ser Leu Tyr
            20
```